(12) United States Patent
Castellvi et al.

(10) Patent No.: US 8,926,667 B2
(45) Date of Patent: Jan. 6, 2015

(54) CONNECTOR

(75) Inventors: Antonio E. Castellvi, Tampa, FL (US);
Scott A. Webb, Clearwater, FL (US);
Craig Corrance, Lake Mary, FL (US);
John Kapitan, Waxhaw, NC (US); Gert Nijenbanning, LZ Hengelo (NL)

(73) Assignee: Transcendental Spine, LLC, Pinellas Park, FL (US)

( * ) Notice: Subject to any disclaimer, the term of this patent is extended or adjusted under 35 U.S.C. 154(b) by 1280 days.

(21) Appl. No.: 12/028,468

(22) Filed: Feb. 8, 2008

(65) Prior Publication Data
US 2008/0195122 A1 Aug. 14, 2008

Related U.S. Application Data

(60) Provisional application No. 60/889,164, filed on Feb. 9, 2007.

(51) Int. Cl.
*A61B 17/70* (2006.01)

(52) U.S. Cl.
CPC ......... *A61B 17/7035* (2013.01); *A61B 17/7041* (2013.01)
USPC .......................................... 606/257; 606/278

(58) Field of Classification Search
USPC .......................... 606/259, 250–257, 260, 278
See application file for complete search history.

(56) References Cited

U.S. PATENT DOCUMENTS

| 5,540,688 | A | 7/1996 | Navas |
|---|---|---|---|
| 5,672,175 | A | 9/1997 | Martin |
| 5,951,555 | A | 9/1999 | Rehak et al. |
| 6,022,350 | A | 2/2000 | Ganem |
| 6,280,443 | B1 | 8/2001 | Gu et al. |
| 6,355,039 | B1 | 3/2002 | Troussel et al. |
| 6,371,957 | B1 | 4/2002 | Amrein et al. |
| 6,402,752 | B2 | 6/2002 | Schaffler-Wachter et al. |
| 6,468,276 | B1 | 10/2002 | McKay |
| 6,554,834 | B1 | 4/2003 | Crozet et al. |
| 6,706,045 | B2 | 3/2004 | Lin et al. |
| 6,755,829 | B1 | 6/2004 | Bono et al. |
| 6,843,791 | B2 | 1/2005 | Serhan |
| 6,869,433 | B2 | 3/2005 | Glascott |
| 6,896,677 | B1 | 5/2005 | Lin |
| 6,916,319 | B2 | 7/2005 | Munting |
| 6,986,771 | B2 | 1/2006 | Paul et al. |
| 6,989,011 | B2 | 1/2006 | Paul et al. |
| 7,137,985 | B2 | 11/2006 | Jahng |
| 2002/0193794 | A1* | 12/2002 | Taylor ............................. 606/61 |
| 2005/0124991 | A1 | 6/2005 | Jahng |
| 2005/0154390 | A1* | 7/2005 | Biedermann et al. ........... 606/61 |
| 2006/0084982 | A1 | 4/2006 | Kim |
| 2006/0129147 | A1 | 6/2006 | Biedermann et al. |
| 2006/0149244 | A1 | 7/2006 | Amrein et al. |
| 2006/0212033 | A1 | 9/2006 | Rothman et al. |

(Continued)

*Primary Examiner* — Eduardo C Robert
*Assistant Examiner* — Julianna N Harvey
(74) *Attorney, Agent, or Firm* — Clements Bernard PLLC; Christopher L. Bernard; Lawrence A. Baratta, Jr.

(57) ABSTRACT

A surgical implant device that controls the relative movement between a first bone or tissue portion and a second bone or tissue portion. The device has a first connector member connected for movement with the first bone or tissue portion and a second connector member connected for movement with the second bone or tissue portion. A biasing member pivotally connects the first connector member to the second connector member and resists the relative rotation between the first connector member and the second connector member.

18 Claims, 21 Drawing Sheets

(56) References Cited

U.S. PATENT DOCUMENTS

| | | |
|---|---|---|
| 2006/0229612 A1 | 10/2006 | Rothman et al. |
| 2006/0264940 A1 | 11/2006 | Hartmann |
| 2006/0282080 A1 | 12/2006 | Albert et al. |
| 2006/0287652 A1 * | 12/2006 | Lessig et al. ............ 606/54 |
| 2007/0032123 A1 * | 2/2007 | Timm et al. ............ 439/395 |
| 2007/0123866 A1 | 5/2007 | Gerbec et al. |
| 2007/0270808 A1 * | 11/2007 | Drewry et al. ............ 606/61 |

* cited by examiner

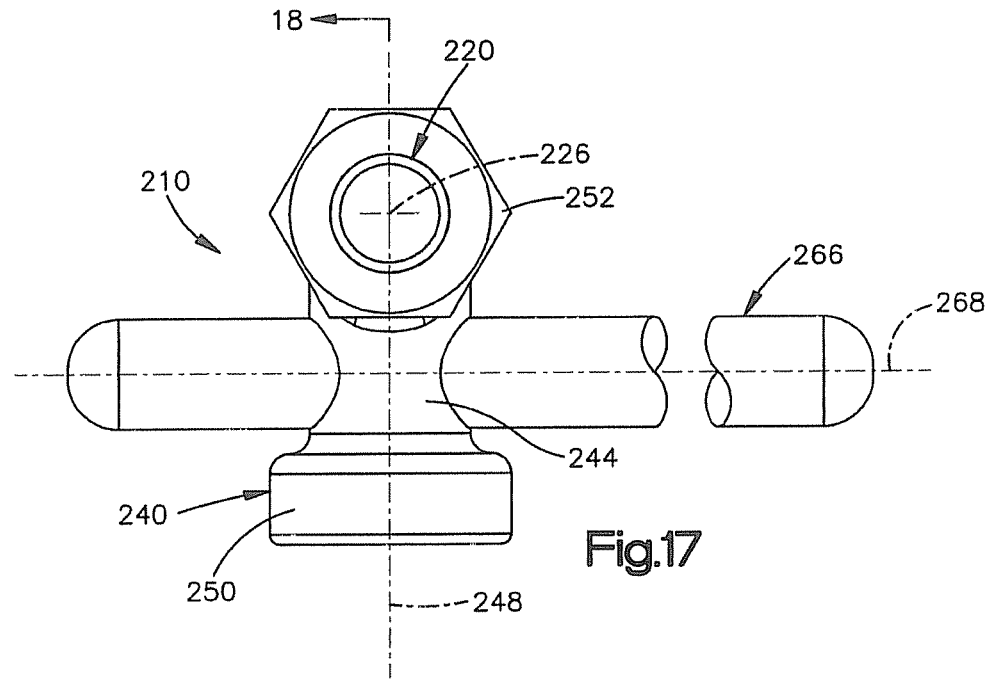
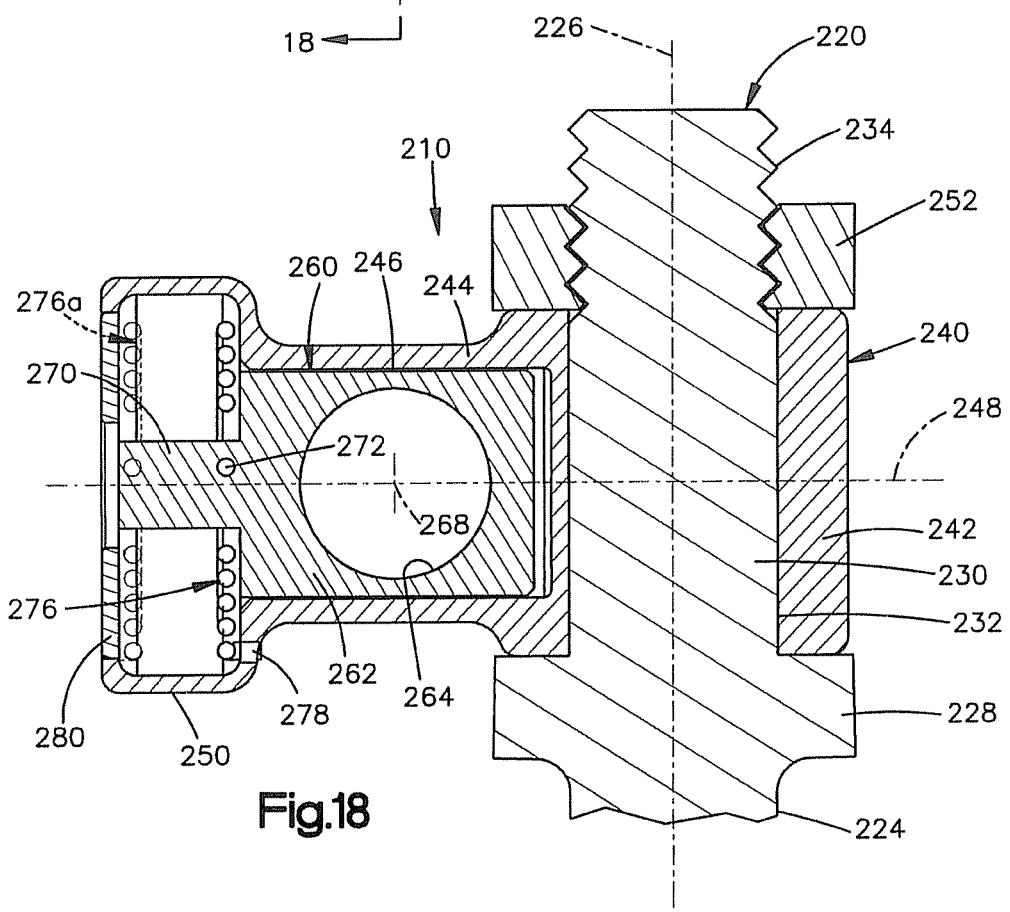

CONNECTOR

RELATED APPLICATIONS

This application claims priority to and incorporates herein by reference, in its entirety, U.S. Provisional Patent Application Ser. No. 60/889,164, filed Feb. 9, 2007.

BACKGROUND

A device or system may be implanted into a patient to provide or enhance stability and quality of motion of the patient. For example, bone implants and systems are used for, among other purposes, control and stabilization of the posterior lumbar spine. In the case of spinal degeneration, for example of a disc or a vertebra, the spine may be unstable, and excess motion may be possible. In such a case, it is known to use a bone implant or system to stabilize the spine while still allowing some controlled motion, or more importantly quality of motion.

Typical spinal systems include pedicle screws that attach to adjacent vertebrae; rigid or semi-rigid rods or plates that extend between the screws of adjacent vertebrae; and connectors for connecting the rods or plates with the screws. Some systems are designed not to allow for any relative movement between vertebrae. Other systems allow for some relative movement between vertebrae, such as via pivotal connectors and/or flexible rods or plates, in an attempt to allow some controlled movement of the spine while still stabilizing the spine.

SUMMARY

The present application describes various embodiments of a device for controlling the relative motion between two objects. The device may include a first connector member, a second connector member, and a biasing member that controls the relative movement between the first connector member and the second connector member. The device is not to be limited to the embodiment(s) shown or described, as they are merely illustrative examples. Thus, the device may be used elsewhere than in the spine, for example, in other orthopedic applications, to connect tissue portions, such as osseous tissue or soft tissue. The application is also directed to a method of use for the device.

Additional features and advantages of the device will be set forth in part in the description that follows, and in part will be obvious from the description, or may be learned by practice of the device. The features and advantages of the device will be realized and attained by means of the elements and combinations particularly pointed out in the appended claims. It is to be understood that both the foregoing general description and the following detailed description are exemplary and explanatory only and are not restrictive of the device, as claimed. The accompanying drawings, which are incorporated in and constitute a part of this specification, illustrate several embodiments of the device, and together with the description, serve to explain the principles of the device.

BRIEF DESCRIPTION OF THE DRAWINGS

In the accompanying drawings, which are incorporated in and constitute a part of the specification, embodiments of the device are illustrated, which, together with a general description of the device given above, and the detailed description given below, serve to exemplify the embodiments of the device:

FIG. 17 is a top view of the connector shown in FIG. 15, wherein the connector is assembled and mounted to a screw;

FIG. 18 is a cross sectional view of the connector shown in FIG. 15, wherein the connector is assembled and mounted to a screw;

DETAILED DESCRIPTION

The present application discloses a device used for controlling motion. The embodiments of the invention illustrate the use of the device in a spinal stabilization and motion preservation system that restricts certain types of motion in an otherwise abnormal or degenerative spine while allowing other types of motion so that the spinal segment is stabilized but not fused. Quantity of motion refers to the range of motion of the spine while quality of motion refers to the characteristics of a rotating vertebra, such as the kinematics.

Figure 1:
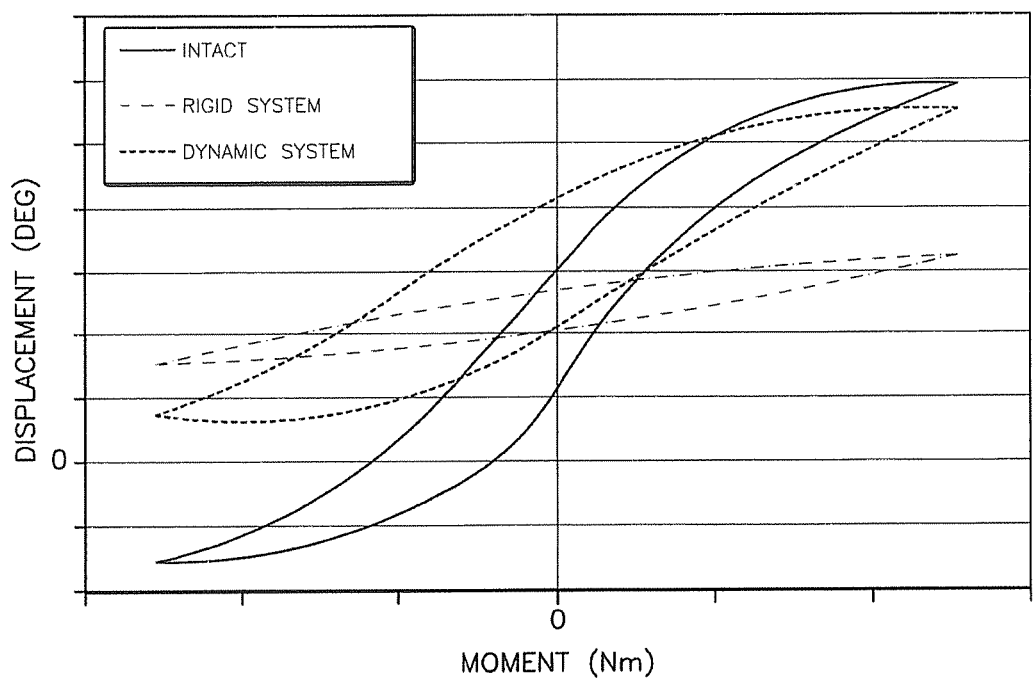
FIG. 1 is an exemplary graph that depicts the motion curves of an intact normal spine and an abnormal or degenerative spine outfitted with various types of rod/connector spinal stabilization systems.

For example, the graph shown in FIG. 1 depicts the motion curves of an intact normal spine and an abnormal or degenerative spine outfitted with either a rigid or dynamic spinal stabilization system. FIG. 1 illustrates that the use of a dynamic spinal stabilization system, for example a dynamic rod and dynamic connector such as the embodiments of the invention illustrated and described herein, allows for a more normal range of motion than the use of a conventional rigid spinal stabilization system.

The y-axis of the graph shown in FIG. 1 represents the displacement (degree of flexion/extension bending) and the x-axis represents the moment (Nm) acting on the vertebral junction. Positive moment values represent flexion (bending forward) while negative moment values represent extension (bending backward). Thus, the moment acting on the vertebral junction increases as a person bends forward (flexion) from a neutral position and decreases as the person returns to the neutral position. Similarly, the moment acting on the vertebral junction increases as a person bends backward (extension) from a neutral position and decreases as the person returns to the neutral position. The total range of motion may be calculated from the total displacement between the top and bottom of the motion curve.

As shown in the graph of FIG. 1, the range of motion of an abnormal or degenerative spine outfitted with a dynamic spinal stabilization system allows for almost as much flexion range of motion as a normal intact spine. Further, an abnormal or degenerative spine outfitted with a dynamic spinal stabilization system allows for an overall greater range of motion than an abnormal or degenerative spine outfitted with a rigid spinal stabilization system. As such, the use of a dynamic spinal stabilizations system, for example a dynamic rod and dynamic connector such as the embodiments of the invention illustrated and described herein, allows for a more normal quantity and quality of motion than the use of a conventional rigid spinal stabilization system.

Although the embodiments of the invention illustrate the use of the device in a spinal stabilization and motion preservation system, the device may be used to control the relative motion between a variety of tissue portions in the body and is not limited to posterior spinal applications. For example, the device may be used in anterior spinal applications or non-spinal applications, such as controlling the relative motion between two bones, such as the pelvis and the femur. In spinal applications, the device may attach to any suitable anatomical feature of a vertebral body, such as for example, the pedicle, lamina, spinous process, or transverse process. Tissue portions, however, are not limited to bone or osseous tissue. Tissue portions may also include soft tissue such as, but not limited to, cartilage or ligaments.

While the embodiments illustrated and described herein are presented in the context of a pivotal connector for controlling the relative motion between two objects having a connector housing (or first connector member), an inner member (or second connector member), and a biasing member controlling the relative movement between the connector housing and the inner member, those skilled in the art will readily appreciate that the device may be used and configured in other ways. For example, the biasing member may be a separate component of the connector. In certain embodiments, the biasing member and the inner member are made from a unitary construction. In other embodiments, the biasing member and the connector housing are made from a unitary construction. In still other embodiments, the biasing member, connector housing, and inner member are made from a unitary construction. Further, the connector may have a stop to limit the relative movement between the connector housing and the inner member.

While various aspects and concepts of the device are described and illustrated herein as embodied in combination in the embodiments, these various aspects and concepts may be realized in many alternative embodiments, either individually or in various combinations and sub-combinations thereof. Unless expressly excluded herein all such combinations and sub-combinations are intended to be within the scope of the device. Still further, while various alternative embodiments as to the various aspects and features of the device, such as alternative materials, structures, configurations, methods, devices, and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the device into additional embodiments within the scope of the device even if such embodiments are not expressly disclosed herein. Additionally, even though some features, concepts or aspects of the device may be described herein as being a preferred arrangement or method, such description is not intended to suggest that such feature is required or necessary unless expressly so stated. Still further, exemplary or representative values and ranges may be included to assist in understanding the device however, such values and ranges are not to be construed in a limiting sense and are intended to be critical values or ranges only if so expressly stated.

It should be noted that for the purposes of this application, the terms attach (attached), connect (connected), and mount (mounted) are not limited to direct attachment, connection, or mounting but also include indirect attachment, connection, or mounting with intermediate parts, components, or assemblies being located between the two parts being attached, connected, or mounted to one another. In addition, the terms attach (attached), connect (connected), and mount (mounted) may include two parts integrally formed or unitarily constructed.

It should also be noted that for the purposes of this application, the term implant (implantable, implanted, etc.) or surgical implant device is not limited to those devices implanted into a bone tissue or soft tissue and completely covered by the skin, but also includes devices implanted into a bone tissue or soft tissue and projecting through the skin.

Figure 2:
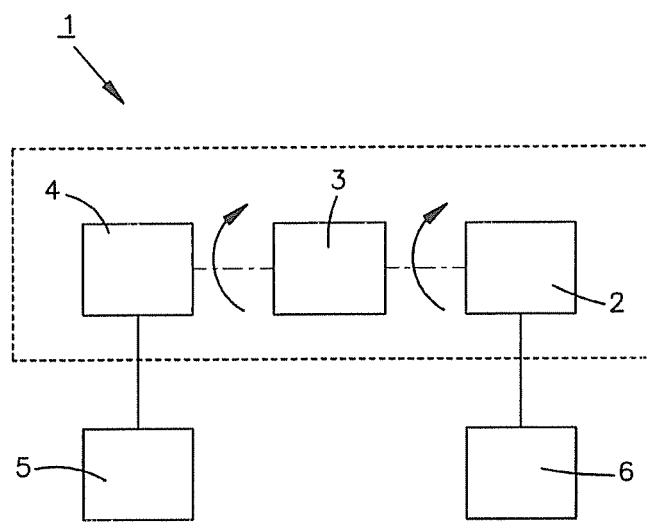
FIG. 2 is a schematic view of a connector according to an embodiment of the invention.

Referring now to the drawings, FIG. 2 is a schematic of a connector 1 according to an embodiment of the invention. Three components of the connector 1 are shown in FIG. 2, the connector housing 2, or first connector member, the biasing member 3, and the inner member 4, or second connector member. The connector housing 2 of the connector 1 attaches to an anchoring device 6. The anchoring device 6 attaches to a first bone portion in the body. The inner member 4 of the connector 1 attaches to a rod or plate 5. The rod or plate 5 generally attaches to an anchoring device attached to a second bone portion of the body. The biasing member 3 controls the relative movement between the connector housing 2 and the inner member 4 by resisting movement of the parts away from a neutral/unloaded or starting position, and biasing the parts back to the neutral/unloaded or starting position. This resistance is provided for movement in both directions of relative rotation.

When the first bone portion moves, force from the first bone portion is transmitted to the anchoring device 6. The force on the anchoring device 6 is transmitted to the connector housing 2 of the connector 1. The connector housing 2 pivots relative to the inner member 4. Thus, the connector housing 2 pivots relative to the rod or plate 5, which is fixed to the inner member 4, allowing the first bone portion to move relative to the second bone portion.

The biasing member 3 resists the relative movement between the connector housing 2 and the rod or plate 5. The biasing member 3 provides an increasing resistance to relative movement between the inner member 4 and the connector housing 2, as the parts move farther. Thus, the biasing member 3 provides an increasing resistance to pivotal movement of the anchoring device 6 relative to the rod or plate 5.

The force applied by the biasing member 3 may increase sufficiently to act as a stop to limit such movement. In addition, portions of the inner member 4 or connector housing 2 may act as a stop to limit the pivotal movement of the anchoring device 6 relative to the rod or plate 5.

When the force on the anchoring device 6 from the first bone portion stabilizes or decreases, the return force of the biasing member 3 acts on the inner member 4 to help bias the parts of the connector 1 back to the starting position.

Figure 3:
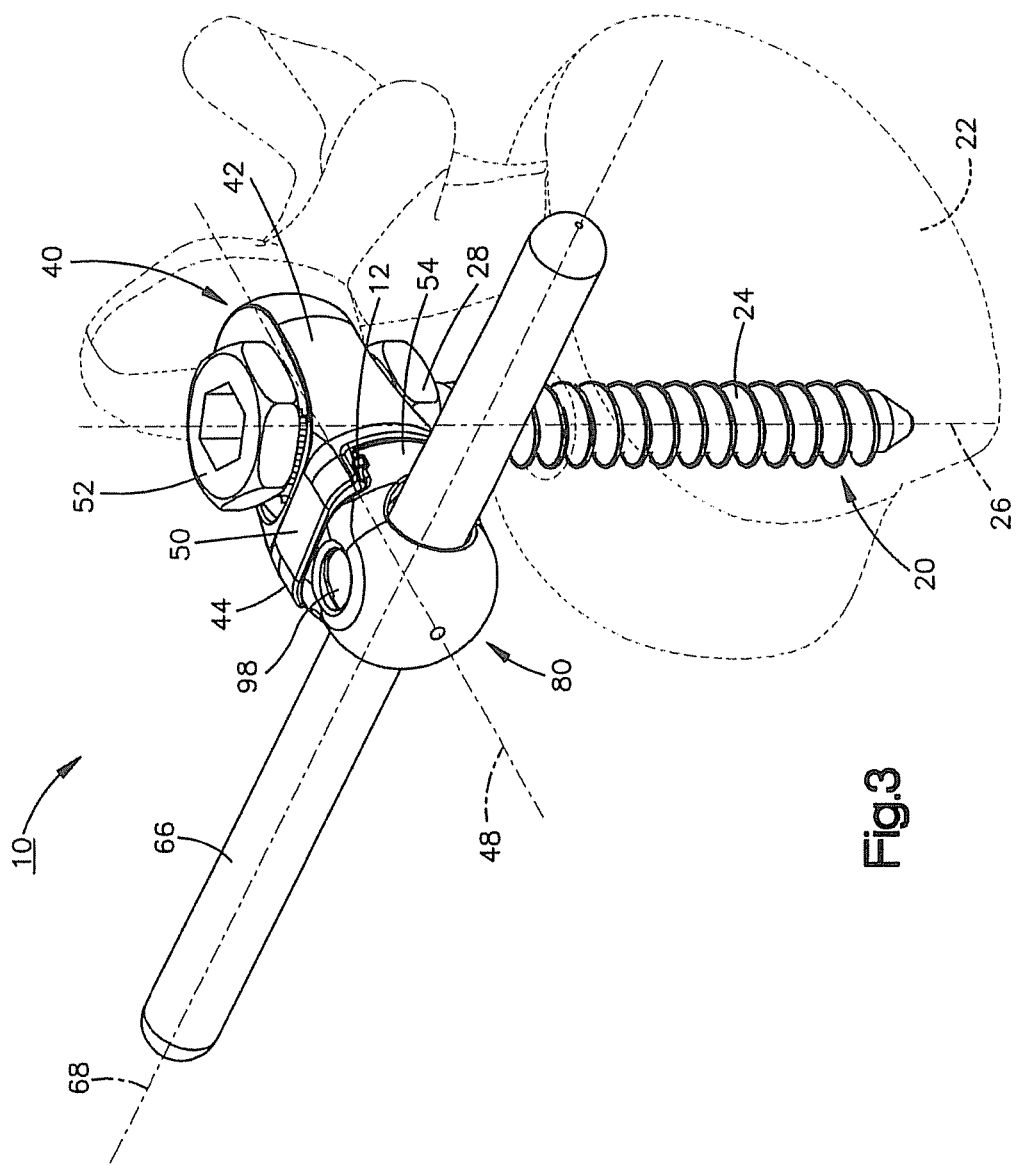
FIG. 3 is a perspective view of a connector according to an embodiment of the invention, wherein the connector is assembled and mounted to a screw.

FIGS. 3-8 illustrate a connector 10 according to an embodiment of the invention. The connector 10 shown in FIG. 3 is adapted to work with a bone screw 20 in a vertebra shown schematically at 22, and with a member, such as a plate or rod, that extends to and connects with another vertebra (not shown) or with another bone tissue or soft tissue portion. The screw 20 (FIG. 3) is a bone screw, or pedicle screw, having a threaded portion 24 centered on an axis 26 of the screw. The screw 20 (FIG. 3), as illustrated, has a flange 28 at the outer end of the threaded portion 24. The flange 28 has wrenching flats for receipt of a tool, such as a spanner or wrench, to grip the screw 20 and drive it into the bone 22. Alternatively, the screw may have a different configuration for helping to drive the screw into the bone 22, for example, a screw head with a hex socket.

Figure 4:
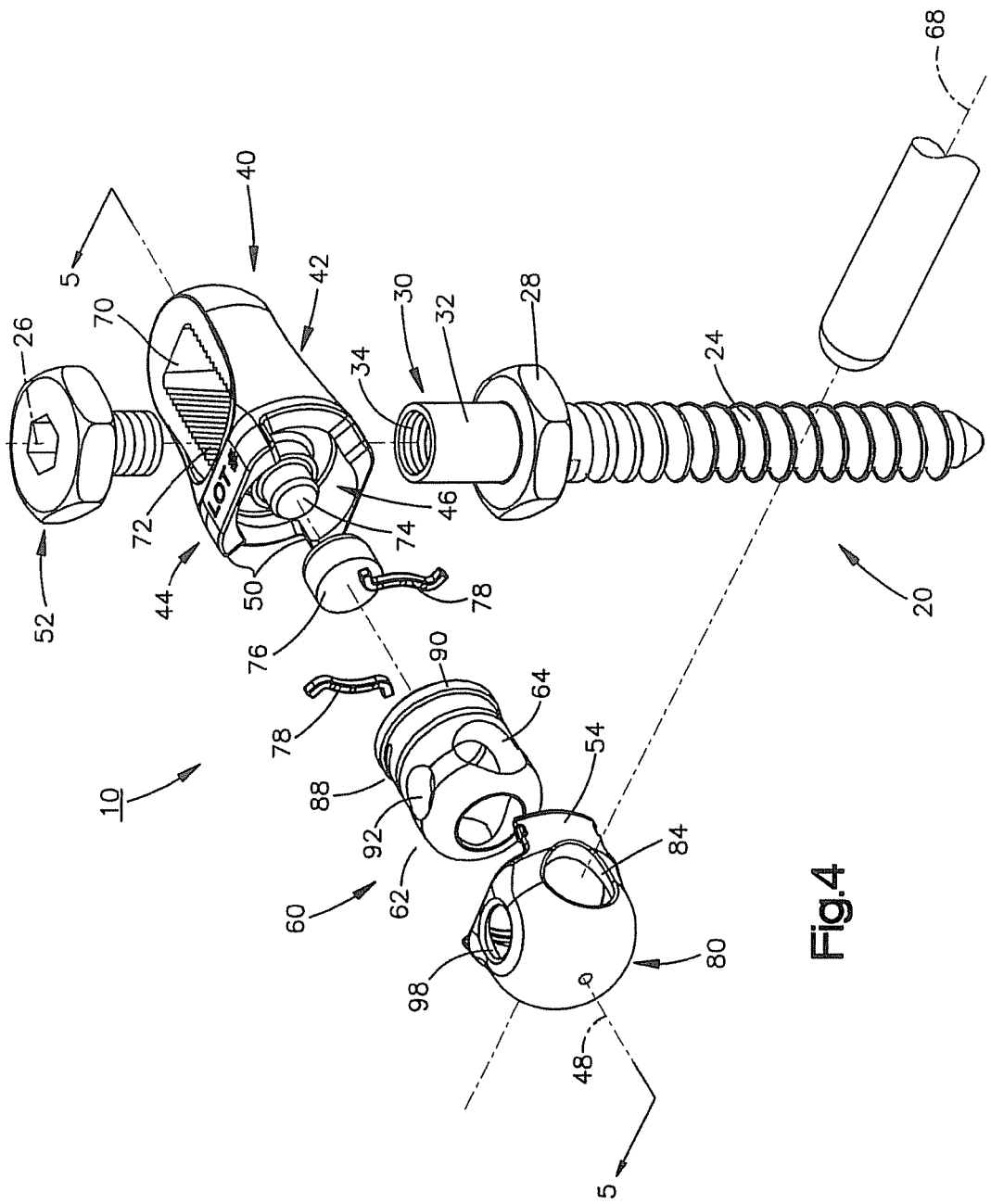
FIG. 4 is an exploded view of the connector shown in FIG. 3.

The screw 20 also includes a mounting portion 30 for mounting or supporting a connector housing 40, or first connector member (FIG. 4). In the illustrated embodiment, the mounting portion 30 has a smooth, cylindrical outer surface 32 centered on the screw axis 26. In other configurations, the mounting portion 30 could have a different shape or surface, such as a threaded configuration or a frusta-conical outer surface. An aperture 34 (FIG. 4) having an interior threaded portion extends into the mounting portion 32. A fastener 52 having a threaded portion and a head communicates with the interior threaded portion of the aperture 34 to secure the connector housing 40 to the screw 20, blocking rotation of the housing about the screw axis 26. As shown, the fastener 52 has a screw head with a hex socket.

The connector housing 40 (FIG. 4) of the connector 10 may be formed as one piece. The connector housing 40 has a mounting sleeve or mounting portion 42 that is received on the mounting portion 30 of the screw 20. The mounting portion 42 of the connector housing 40 supports the connector housing on the screw 20 for pivotal movement relative to the screw about the screw axis 26, before the connector housing is tightened down on the screw. As shown, the mounting portion 42 has an elongated aperture 70 with interior grooves 72 that allow the mounting portion 42 of the connector housing 40 to hold the mounting portion 30 of the screw 20, preventing rotation of the connector housing relative to the screw. As noted above, in other configurations, the mounting portion of the screw could have a different shape or surface that still allows for the connector housing to be positioned relative to the screw before being tightened down. Further, the mounting portion of the connector housing may also have a different shape or surface, such as a threaded configuration or a more rounded aperture.

A biasing member support portion 44 of the connector housing 40 is movable with the mounting portion 42 and extends outward from the mounting portion 42 (FIG. 4). The biasing member support portion 44 has a chamber 46 centered on a pivot axis 48 of the connector 10. In the illustrated embodiment, the chamber 46 is cylindrical. In addition, the biasing member support portion 44 has two projections 50. The two projections 50, or teeth, extend outward from the edge of the chamber 46, in a direction away from the mounting portion 42 of the connector housing 40. However, in certain embodiments, the biasing member support portion 44 may have more or less projections.

The biasing member support portion 44 of the connector housing 40 also has a shaft 74 centered on the pivot axis 48 of the connector 10 (FIG. 4). The shaft 74 communicates with a bore 96 (FIG. 5) of a biasing member portion 88 of an inner member 60 of the connector 10 (described below). The shaft 74 supports an end 90 of the biasing member portion 88 inserted into the chamber 46 of the connector housing 40. As shown, the shaft 74 is a stepped shaft having the narrow portion at the end farthest from the connector housing 40.

A cap 76 covers the narrow end of the stepped shaft 74 and helps support the biasing member portion 88 of the inner member 60. The cap 76 may also rotate relative to the shaft 74 as the connector housing 40 pivots relative to the inner member 60.

The inner member 60, or second connector member, of the connector 10 is generally cylindrical and has two portions, a rod support portion 62 and the biasing member 88 portion (FIG. 4). The biasing member portion 88 is closely received in the chamber 46 of the connector housing 40. In the illustrated embodiment, the end 90 of the biasing member portion 88 is inserted in the chamber 46 of the connector housing 40 and welded, such as by laser welding. However, the end 90 of the biasing member portion 88 may be connected to the connector housing 40 by any suitable means known in the art, such as with a threaded connection, setscrew, press fit, or adhesive.

A bore 64 extends radially through the rod support portion 62 of the inner member 60 and is adapted to receive a rod 66 therethrough (FIG. 4). The bore 64 defines a rod axis 68 of the connector 10. In the illustrated embodiment, the inner member 60 has set screw threads 92 for securing the rod 66 in the bore 64 of the inner member 60 to prevent the rod 66 from rotating or moving axially within the inner member 60. However, the rod 66 may be secured in the bore 64 by any suitable means known in the art, such as with a cotter pin or press fit.

The biasing member 88 of the inner member 60 resists the rotation of the connector housing 40 relative to the inner member 60 and helps to bias the parts of the connector 10 back to a starting position. As illustrated, the biasing member 88 and the inner member 60 are a unitary construction. The biasing member 88 is formed from a spiral cut in the inner member 60 between the end 90 and the rod support portion 62. However, other types of biasing members may be used, such as for example an elastic connection or torsion bar. Further, in other embodiments (not shown), the connector housing and the biasing member are a unitary construction. In these embodiments, the biasing member may be formed from a spiral cut in a portion of the connector housing extending outward from the mounting portion.

Figure 5:
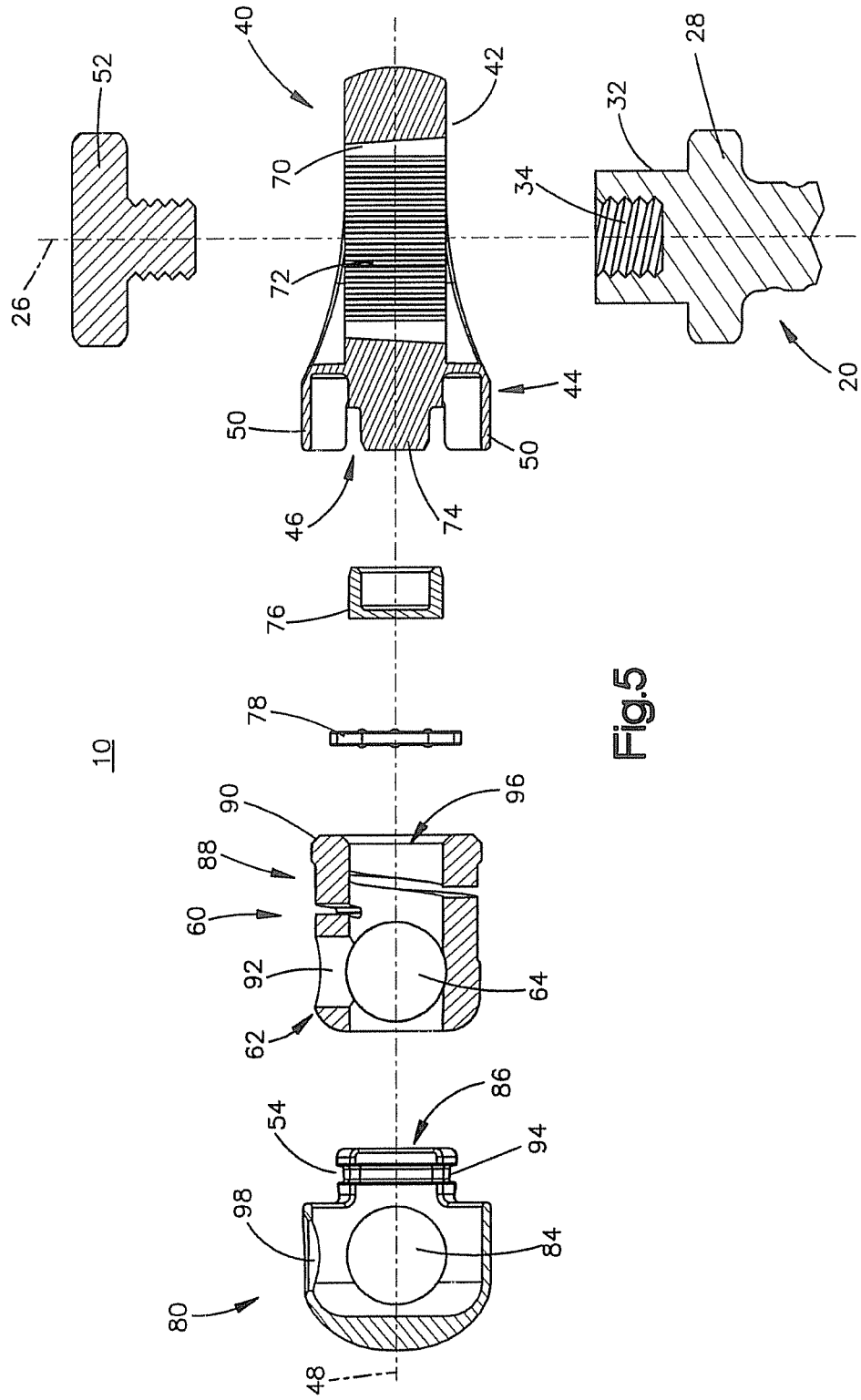
FIG. 5 is a exploded cross sectional view of the connector shown in FIG. 3.
Figure 6:
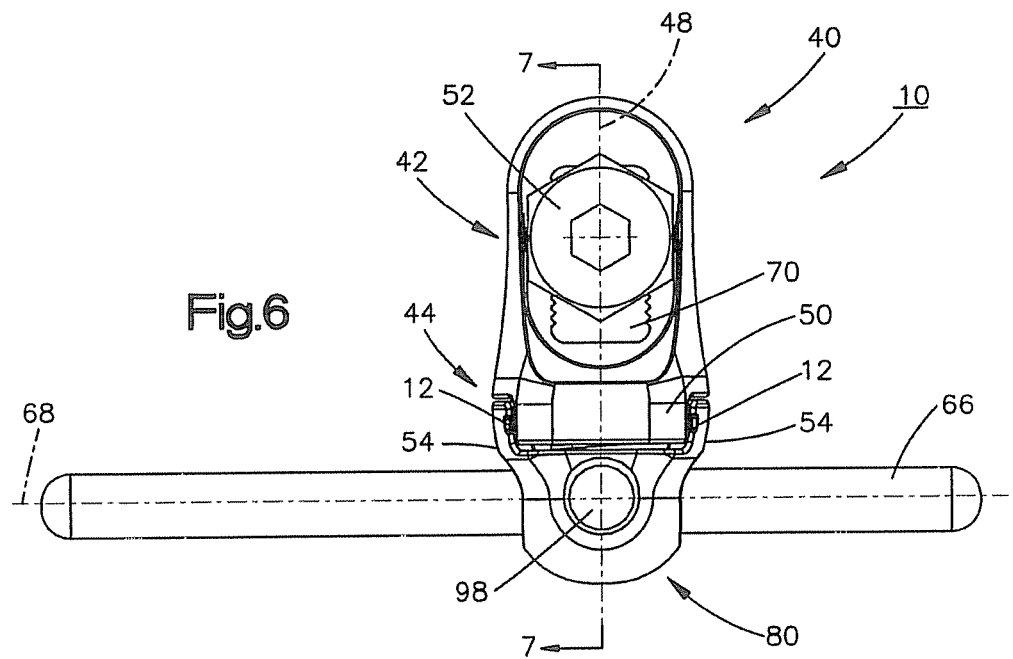
FIG. 6 is a top view of the connector shown in FIG. 3, wherein the connector is assembled and mounted to a screw.
Figure 7:
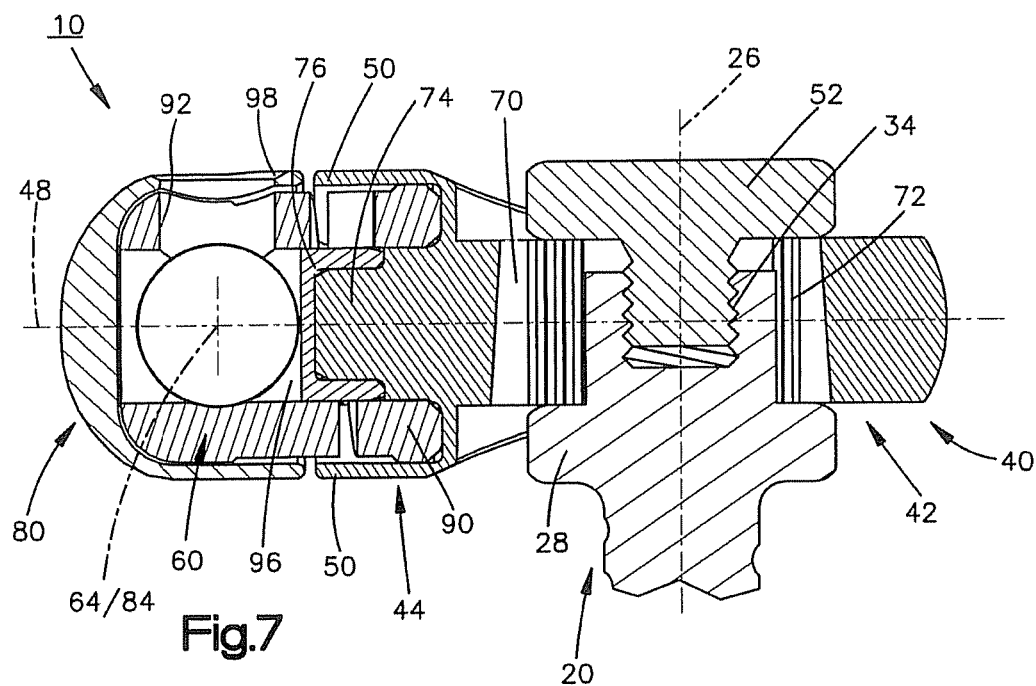
FIG. 7 is a cross sectional view of the connector shown in FIG. 3, wherein the connector is assembled and mounted to a screw.

The biasing member 88 also has a bore 96 (FIG. 5). As shown, the bore 96 is centered on the pivot axis 48 and extends generally from the end 90 to the rod support portion 62 of the inner member 60. The size and shape of the bore 96 affect the biasing member's resistance. In general, a larger bore provides less resistance while a smaller bore provides greater resistance. In certain embodiments, however, the biasing member does not have a bore.

The connector 10 further includes an outer member 80. In certain embodiments, the outer member 80 is optional. In addition, the outer member 80 and the inner member 60 may be a unitary construction. As illustrated, the outer member 80 has a chamber 86 centered on the pivot axis 48 of the connector 10. The chamber 86 is cylindrical and receives the rod support portion 62 of the inner member 60. Similar to the inner member 60, a bore 84 extends radially through the outer member 80 and is adapted to receive the rod 66 (FIG. 3) therethrough. The bore 84 is centered on the rod axis 68 of the connector 10.

Further, the outer member 80 has an aperture 98 for securing the outer member 80 to the inner member 60. In the illustrated embodiment, the aperture 98 is generally aligned with the setscrew threads 92 of the inner member 60. A setscrew, inserted through the aperture 98 and into the inner member 60, prevents the outer member 80 from rotating or moving axially relative to the inner member 60. However, the outer member 80 may be secured to the inner member 60 by any suitable means known in the art, such as with a cotter pin or press fit.

As illustrated, the outer member 80 has two projections 54. The two projections 54, or teeth, extend from the edge of the chamber 86 in a direction toward the connector housing 40. However, in certain embodiments, the outer member 80 may have more or less projections. In the illustrated embodiment, the projections 54 of the outer member 80 are adapted such that they loosely mate with the projections 50 of the connector housing 40 (FIG. 3). As a result, the projections 50 of the connector housing 40 will interfere with the projections 54 of the outer member 80 as the connector housing 40 rotates relative to the outer member 80. This interference of the projections 50, 54 creates a stop to the relative movement between the connector housing 40 and the inner member 60. The range of rotation of the connector housing 40 relative to the inner member 60 will vary depending on various factors. For example, the number, size, and shape of the projections 50, 54 may vary such that the spacing between the projections 50, 54 changes, creating different ranges of rotation. Further, one or both sets of projections 50, 54 may include a different material, such as an elastic material, that "cushions" the interference of the projections 50, 54.

As stated earlier, some embodiments do not include the outer member. Removal of the outer member decreases the overall size of the connector in applications where decreased size is beneficial. In these embodiments, the connector housing 40 and the inner member 60 may not have external projections that interfere to create a stop to the relative movement between the connector housing and the inner member, such as external projections 50, 54 in FIG. 4. Instead, the force applied by the biasing member 88 may increase sufficiently to act as a stop to limit such movement. Further, in certain embodiments, a stop may be internal to the connector, for example the embodiment of the invention depicted in FIGS. 20-27. In other embodiments of the invention, an internal first stop, such as a projection or groove, within the bore 96 of the biasing member 88 may interfere with an internal second stop on the shaft 74 of the biasing member support portion 44. This interference may create a stop to the relative movement between the connector housing 40 and the inner member 60.

In the illustrated embodiment, a set of bands 78 act as soft stops to cushion the interference of the projections 50, 54 (FIG. 4). As shown, the bands 78 seat in channels 94 (FIG. 5) along the interior of the projections 54 of the outer member 80, trapping the bands between the inner member 60 and the outer member. As the connector housing 40 pivots relative to the outer member 80, the ends 12 of the bands 78 are pinched between the projections 54 of the outer member and the projections 50 of the connector housing, creating a soft stop. The bands 78 may be made of any suitable implantable material that "cushions" the interference of the projections 50, 54, such as polyurethane.

As illustrated, the connector housing 40, inner member 60, and outer member 80 are made from titanium or a titanium alloy. However, some or all of the connector 10 components may be made from a variety of materials that are suitable for mammalian implantation, such as for example, but not limited to, polyethylene or polyurethane. Further, the screw 20 and the rod 66 may be made from a variety of materials that are suitable for mammalian implantation, such as titanium or a titanium alloy.

As described below, the biasing member 88 of the inner member 60 provides resistance to relative rotation between the inner member and the connector housing 40, resisting movement of the parts away from a neutral/unloaded or starting position, and biasing the parts back to the neutral/unloaded or starting position. This resistance is provided for movement in both directions of relative rotation, as shown by the arrows 82 and 84 in FIG. 8.

Figure 8:
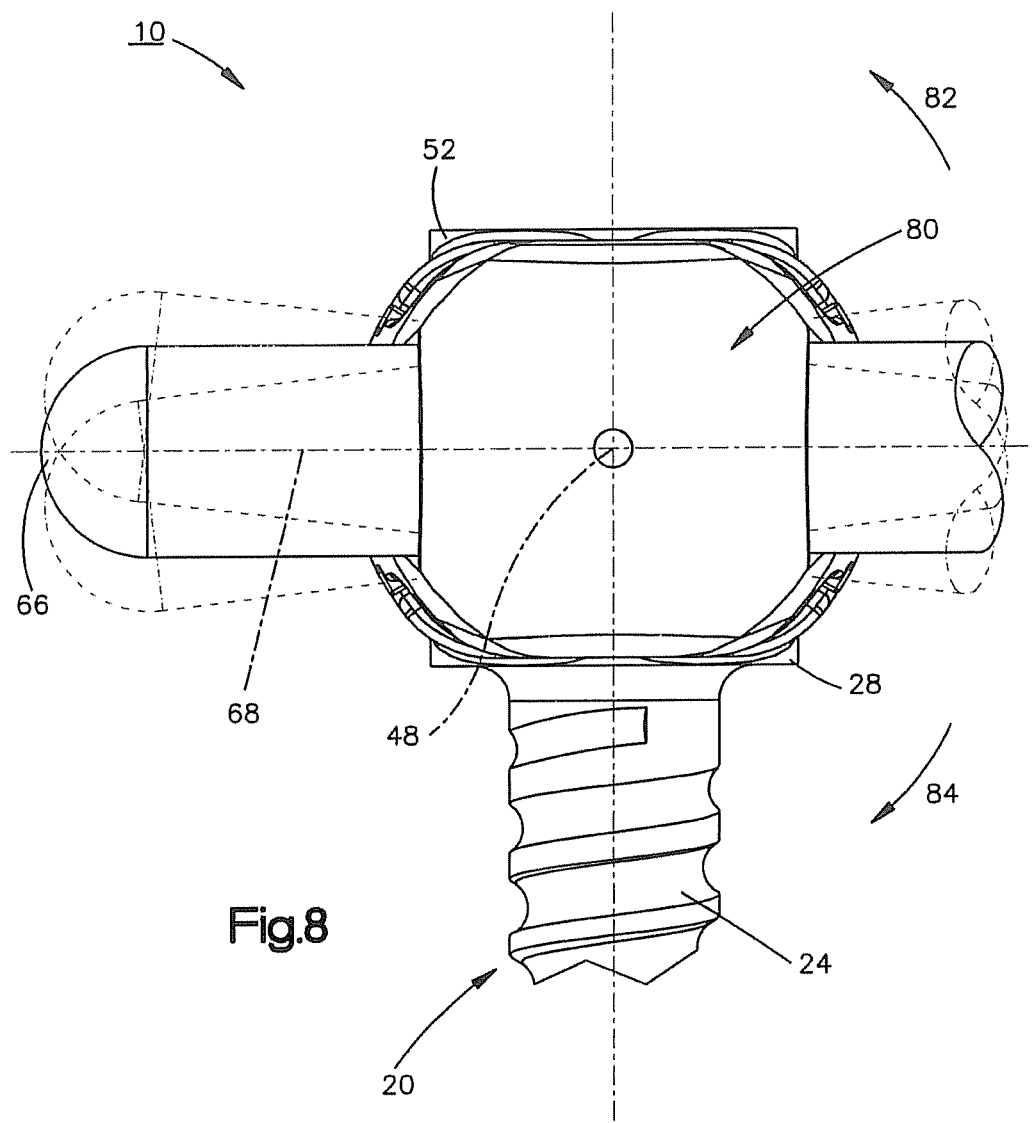
FIG. 8 is a front view of the connector shown in FIG. 3, wherein the connector is assembled and mounted to a screw.

Specifically, when the spine is flexed or extended, the vertebra 22 moves relative to the rod 66—for example, in a first direction as shown by the arrow 82 in FIG. 8. Force from the vertebra 22 is transmitted to the screw 20. The force on the screw 20 is transmitted to the connector housing 40. The connector housing 40 pivots relative to the rod support portion 62 of the inner member 60, about the pivot axis 48. Thus, the connector housing 40 pivots relative to the rod 66, which is fixed to the inner member 60.

The biasing member 88 resists the relative movement between the connector housing 40 and the rod 66, about the axis 48, in the first direction shown by the arrow 82. The biasing member 88 provides an increasing resistance to relative movement between the inner member 60 and the connector housing 40, as the parts move farther. Thus, the biasing member 88 provides an increasing resistance to pivotal movement of the screw 20 relative to the rod 66.

The force applied by the biasing member 88 may increase sufficiently to act as a stop to limit such movement. As stated earlier, the interference of the projections 50, 54 may also act as a stop to limit the pivotal movement of the screw 20 relative to the rod 66. Finally, the bands 78 may act as soft stop to cushion the interference of the projections 50, 54.

When the force on the screw 20 from the patient stabilizes or decreases, the return force of the biasing member 88 acts on the inner member 60 to help bias the parts of the connector 10 back to the starting position, in the direction indicated by the arrow 84 in FIG. 8. Further, a return force provided by the bands 78 may act on the projections 50, 54 to help bias the parts of the connector 10 back to the starting position.

The connector 10 may be configured to allow any desired range of movement within the physical constraints of the connector and associated devices. As one example, the connector 10 may be configured to allow for up to 2 or 3 degrees of movement in either direction from the starting or neutral/unloaded position.

The amount of resistance and return force provided by the connector 10 may be adjusted by removing the inner member 60 and replacing it with an inner member having a stiffer or softer biasing member. The connector 10 as shown may also be interchanged with another connector of the same or a different type, simply by removing the fastener 52 and pulling the connector housing 40 axially off the screw 20.

Figure 9:
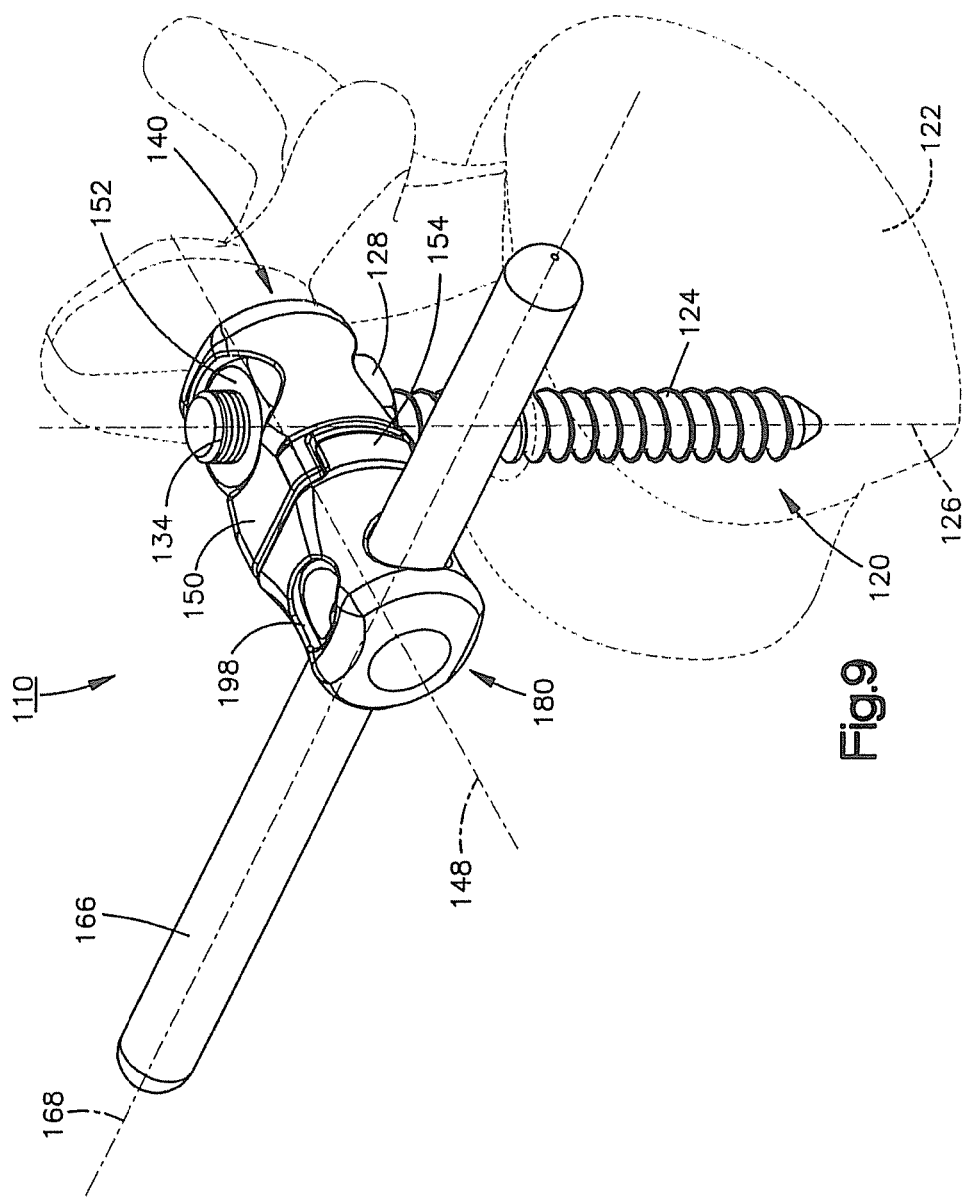
FIG. 9 is a perspective view of a connector according to another embodiment of the invention, wherein the connector is assembled and mounted to a screw.

FIGS. 9-14 illustrate another embodiment of the invention similar to the embodiment depicted in FIGS. 3-8. The connector 110 shown in FIG. 9 is adapted to work with a bone screw 120 in a vertebra shown schematically at 122, and with a member, such as a plate or rod, that extends to and connects with another vertebra (not shown) or with another bone tissue or soft tissue portion.

Figure 10:
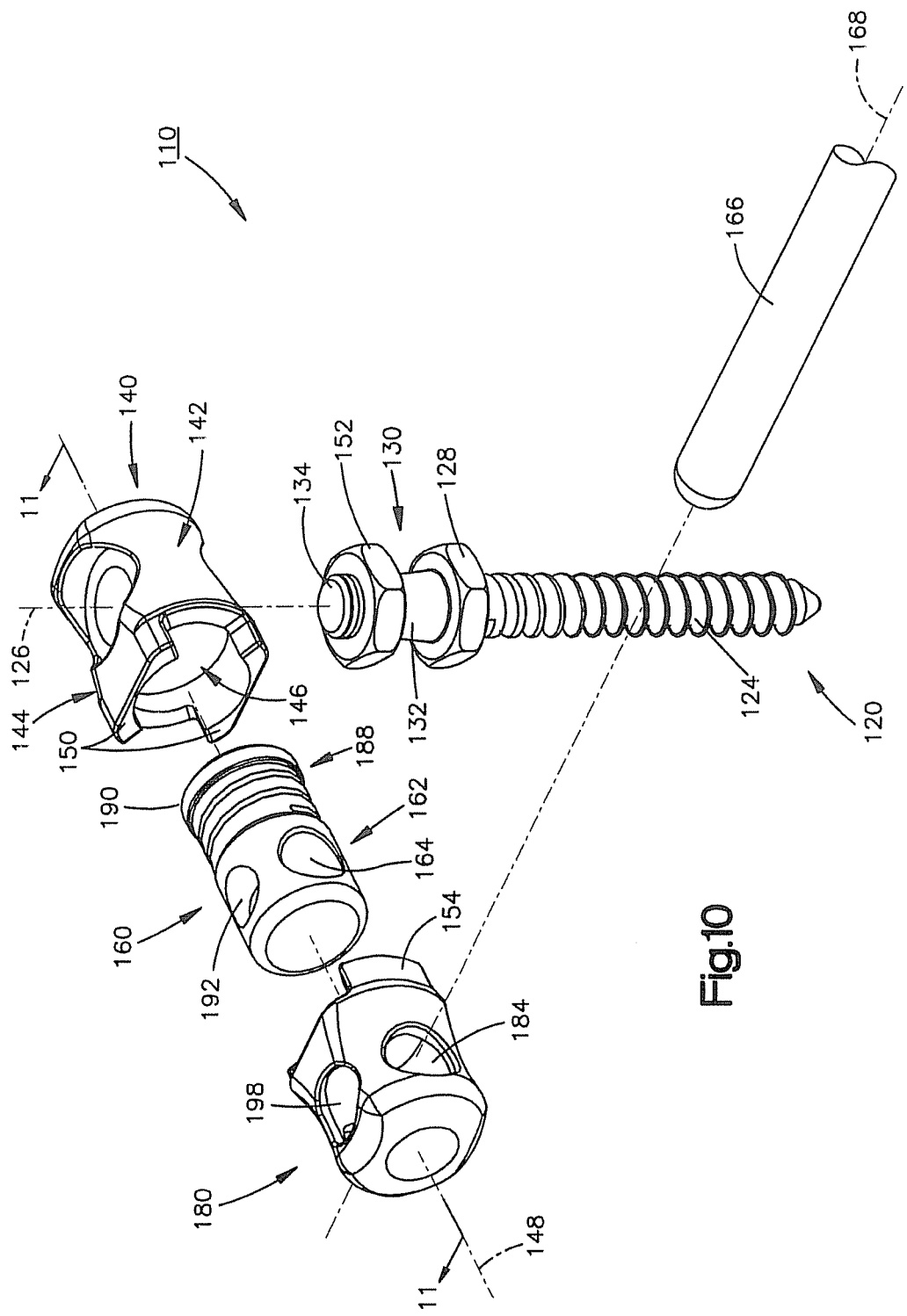
FIG. 10 is an exploded view of the connector shown in FIG. 9.
Figure 11:
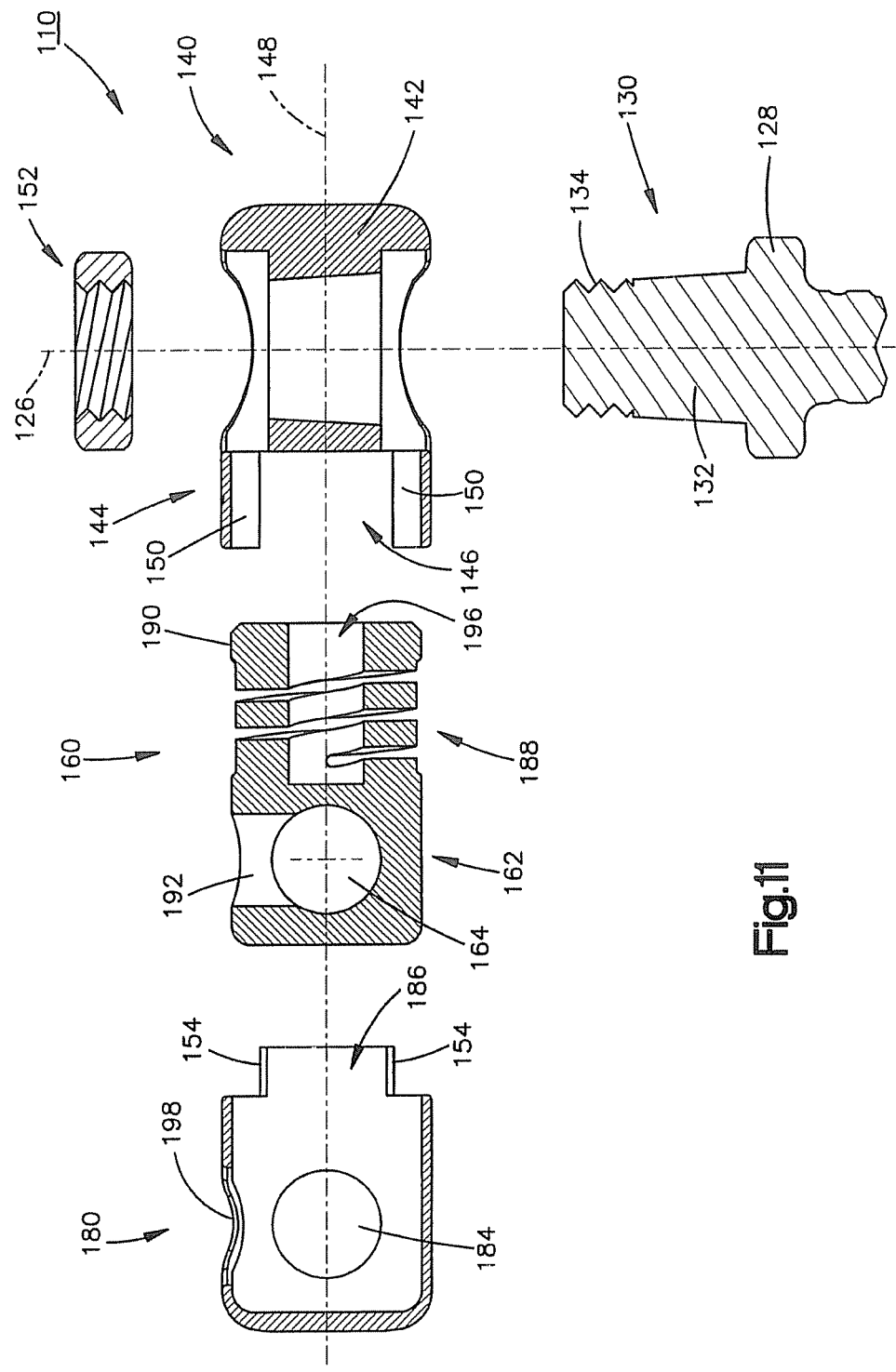
FIG. 11 is a exploded cross sectional view of the connector shown in FIG. 9.
Figure 12:
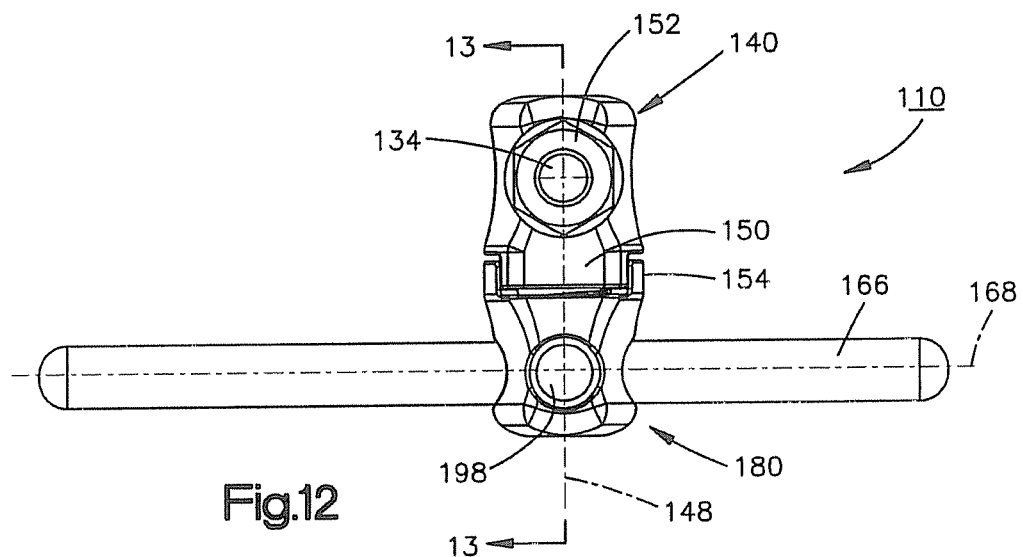
FIG. 12 is a top view of the connector shown in FIG. 9, wherein the connector is assembled and mounted to a screw.
Figure 13:
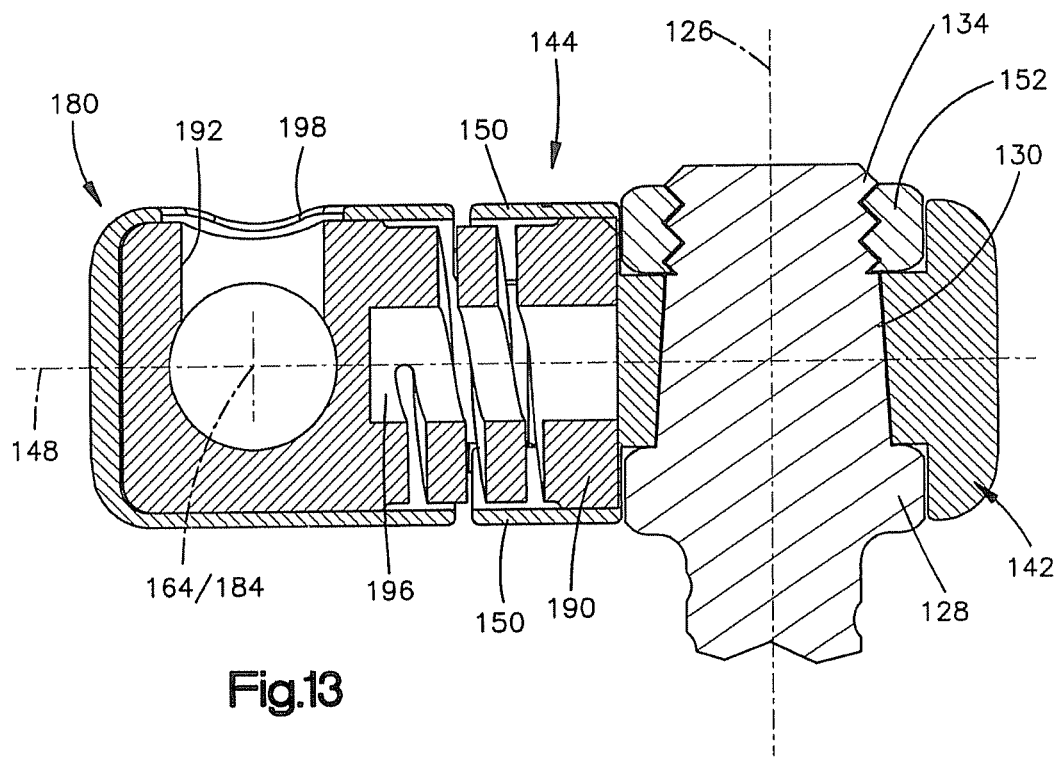
FIG. 13 is a cross sectional view of the connector shown in FIG. 9, wherein the connector is assembled and mounted to a screw.
Figure 14:
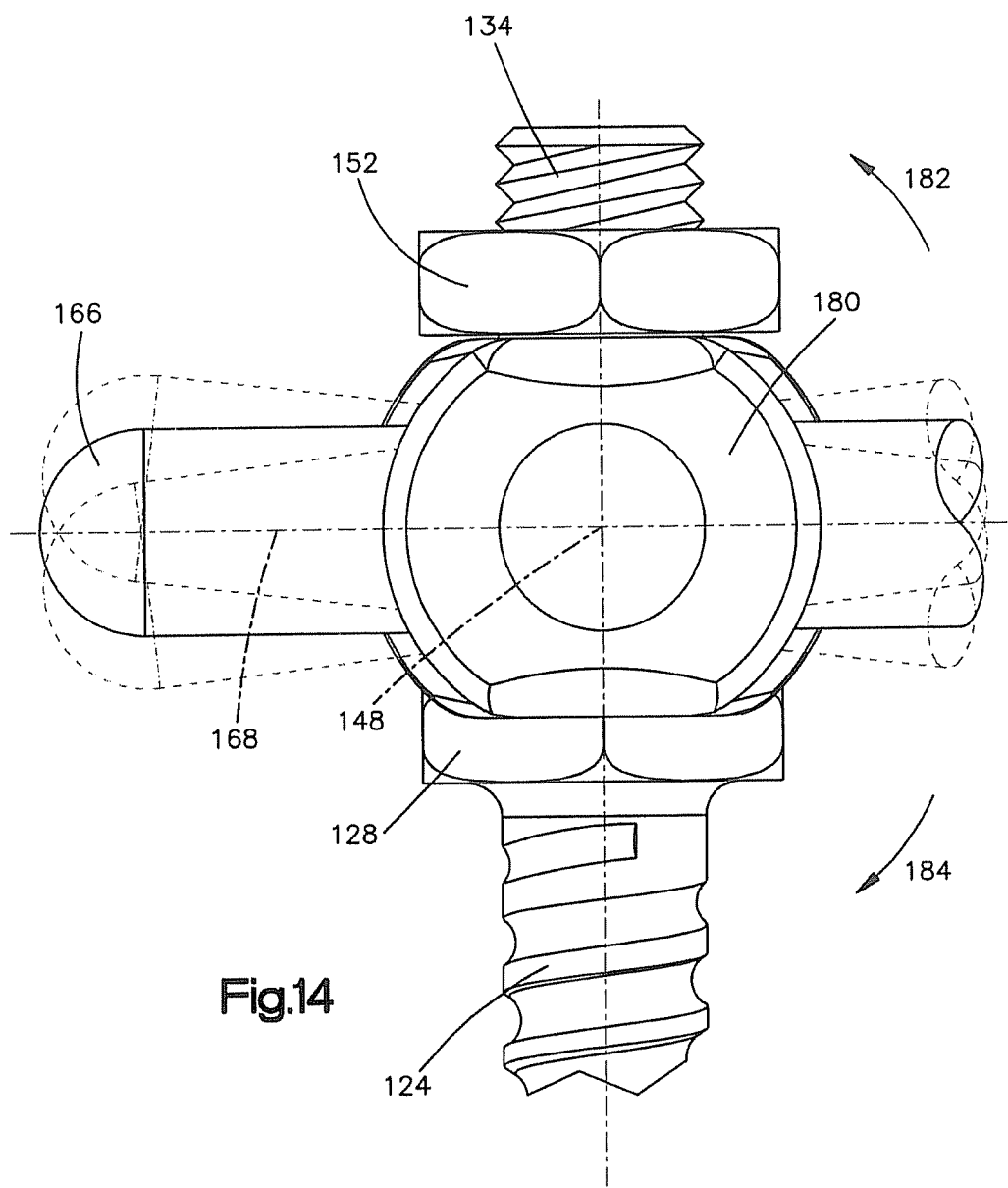
FIG. 14 is a front view of the connector shown in FIG. 9, wherein the connector is assembled and mounted to a screw.

The screw 120 (FIG. 9) is a bone screw, or pedicle screw, having a first threaded portion 124 centered on an axis 126 of the screw. The screw 120 (FIG. 10), as illustrated, has a flange 128 at the outer end of the first threaded portion 124. The flange 128 has wrenching flats for receipt of a tool, such as a spanner or wrench, to grip the screw 120 and drive it into the bone 122. The screw 120 also includes a mounting portion 130 for mounting or supporting a connector housing 140, or first connector member (FIG. 10). In the illustrated embodiment, the mounting portion 130 has a smooth frusta-conical outer surface 132 centered on the screw axis 126. A second threaded portion 134 (FIG. 11) of the screw 120 extends outward from the mounting portion 132. A nut 152 is screwed on the second threaded portion 134 of the screw 120 to secure the connector housing 140 to the screw, blocking rotation of the connector housing about the screw axis 126.

The connector housing 140 (FIG. 10) of the connector 110 has a mounting sleeve or mounting portion 142 that is received on the mounting portion 130 of the screw 120. The mounting portion 142 of the connector housing 140 supports the connector housing on the screw 120 for pivotal movement relative to the screw about the screw axis 126, before the connector housing is tightened down on the screw. A biasing member support portion 144 of the connector housing 140 is movable with the mounting portion 142 and extends outward from the mounting portion 142 (FIG. 10). The biasing member support portion 144 has a chamber 146 centered on a pivot axis 148 of the connector 110. In the illustrated embodiment, the chamber 146 is cylindrical. In addition, the biasing member support portion 144 has two projections 150. The two projections 150, or teeth, extend outward from the edge of the chamber 146, in a direction away from the mounting portion 142 of the connector housing 140.

The connector 110 further includes an inner member 160, or second connector member. In the illustrated embodiment, the inner member 160 is generally cylindrical and has a rod support portion 162 and a biasing member 188. The biasing member 188 is closely received in the chamber 146 of the connector housing 140. In the illustrated embodiment, an end 190 of the biasing member 188 is inserted in the chamber 146 of the connector housing 140 and welded, for example such as laser welding.

A bore 164 extends radially through the rod support portion 162 of the inner member 160 and is adapted to receive a rod 166 (FIG. 10) therethrough. The bore 164 defines a rod axis 168 of the connector 110. In the illustrated embodiment, the inner member 160 has set screw threads 192 for securing the rod 166 in the bore 164 of the inner member 160 to prevent the rod 166 from rotating or moving axially within the inner member 160.

The biasing member 188 of the inner member 160 resists the rotation of the connector housing 140 relative to the inner member 160 and helps to bias the parts of the connector 110 back to a starting position. As illustrated, the biasing member 188 and the inner member 160 are a unitary construction. The biasing member 188 is formed from a spiral cut in the inner member 160 between the end 190 and the rod support portion 162. The biasing member 188 also has a bore 196. As shown, the bore 196 is centered on the pivot axis 148 and extends generally from the end 190 to the rod support portion 162 of the inner member 160.

The connector 110 further includes an outer member 180. As illustrated, the outer member 180 has a chamber 186 centered on the pivot axis 148 of the connector 110. The chamber 186 is cylindrical and receives the rod support portion 162 of the inner member 160. Similar to the inner member 160, a bore 184 extends radially through the outer member 180 and is adapted to receive the rod 66 (FIG. 10) therethrough. The bore 184 is centered on the rod axis 168 of the connector 110. Further, the outer member 180 has an aperture 198 for securing the outer member 180 to the inner member 160. In the illustrated embodiment, the aperture 198 is generally aligned with the setscrew threads 192 of the inner member 160. A setscrew, inserted through the aperture 198 and into the inner member 160, prevents the outer member 180 from rotating or moving axially relative to the inner member 160.

As illustrated, the outer member 180 has two projections 154. The two projections 154, or teeth, extend from the edge of the chamber 186 in a direction toward the connector housing 140. In the illustrated embodiment, the projections 154 of the outer member 180 are adapted such that they loosely mate with the projections 150 of the connector housing 140 (FIG. 9). As a result, the projections 150 of the connector housing 140 will interfere with the projections 154 of the outer member 180 as the connector housing 140 rotates relative to the outer member 180. This interference of the projections 150, 154 creates a stop to the relative movement between the connector housing 140 and the inner member 160.

Similar to the connector 10 depicted in FIGS. 3-8, the biasing member 188 of the connector 110 provides resistance to relative rotation between the inner member 160 and the connector housing 140, resisting movement of the parts away from a neutral/unloaded or starting position, and biasing the parts back to the neutral/unloaded or starting position. This resistance is provided for movement in both directions of relative rotation, as shown by the arrows 182 and 184 in FIG. 14. The connector 110 may be configured to allow any desired range of movement within the physical constraints of the connector and associated devices.

Figure 15:
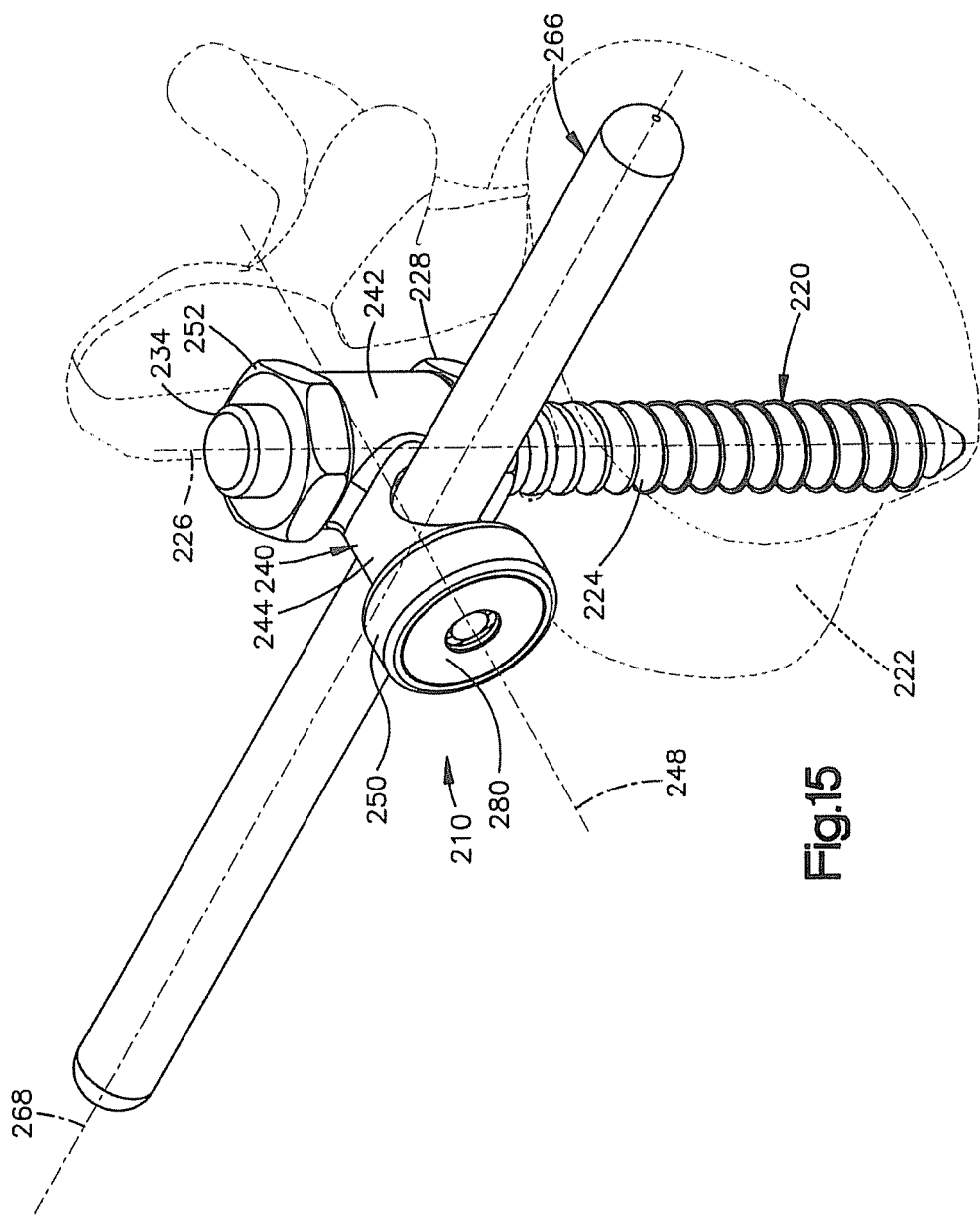
FIG. 15 is a perspective view of a connector according to another embodiment of the invention, wherein the connector is assembled and mounted to a screw.
Figure 16:
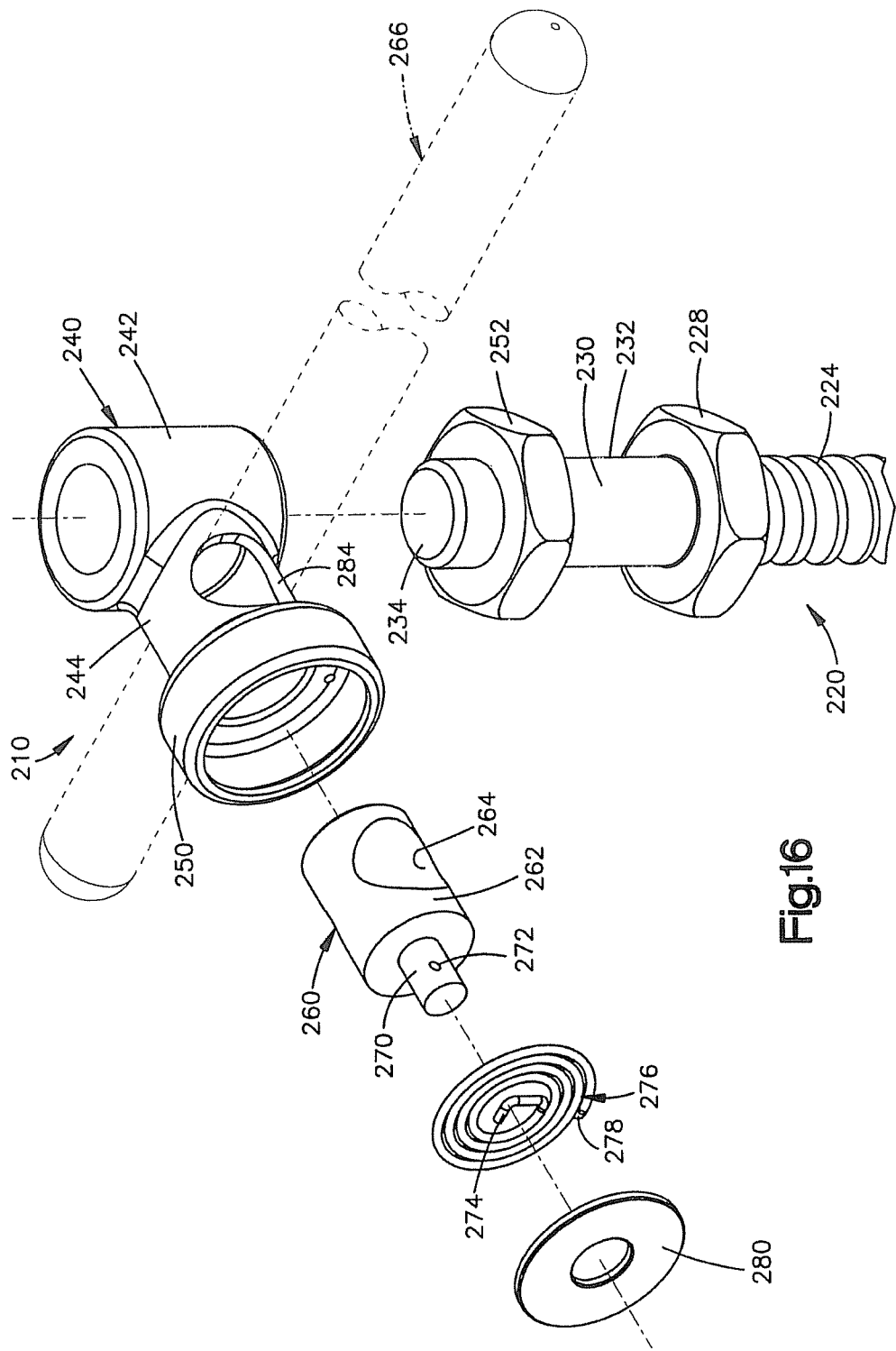
FIG. 16 is an exploded view of the connector shown in FIG. 15.

FIGS. 15-19 depict a connector 210 according to another embodiment of the device. Similar to the connector 110 shown in FIGS. 9-14, the connector 210 shown in FIG. 15 is adapted to work with a bone screw 220 in a vertebra shown schematically at 222, and with a member, such as a plate or rod, that extends to and is connected with another vertebra (not shown) or with other bone tissue or soft tissue portion.

The connector 210 includes a connector housing 240 (FIG. 16), or first connector member, that may be formed as one piece. The connector housing 240 has a mounting sleeve or mounting portion 242 that is received on the mounting portion 230 of the screw 220. The mounting portion 242 of the connector housing 240 supports the connector housing on the screw 220 for pivotal movement relative to the screw about the screw axis 226, before the connector housing is tightened down on the screw. In other configurations, the mounting portion of the screw could have a different shape or surface, such as a threaded configuration, that still allows for the connector housing to be positioned relative to the screw before being tightened down. Further, the mounting portion of the connector housing may also have a different shape or surface, such as a threaded configuration.

A rod support portion 244 of the connector housing 240 is movable with the mounting portion 242 and extends outward from the mounting portion. The rod support portion 244 has a cylindrical chamber 246 centered on a pivot axis 248 of the connector. The connector housing 240 also has a biasing member housing portion 250 that is disposed outward of the rod support portion 244. In other embodiments, the biasing member housing portion of the connector housing could be located inward of the rod support portion. A nut 252 is screwed on the second threaded portion 234 of the screw 220 to secure the connector housing 240 to the screw, blocking rotation of the connector housing about the screw axis 226.

The connector 210 further includes an inner member 260, or second connector member. The inner member 260 is a generally cylindrical member that has a cylindrical rod support portion 262 closely received in the chamber 246 of the connector housing 240. The inner member 260 is thus supported in the connector housing 240, for rotation relative to the connector housing, about the pivot axis 248.

A bore 264 extends radially through the rod support portion 262 of the inner member 260 and is adapted to receive a rod 266 therethrough. The bore 264 defines a rod axis 268 of the connector 210.

A biasing member receiving portion 270 of the inner member 260 extends outward from the rod support portion 262. The biasing member receiving portion 270 has an opening 272 for receiving the inner end 274 of a biasing member 276 (FIG. 16), as described below. The inner member 260 may have setscrew threads or other means (not shown) for securing the rod 266 in the bore 264 of the inner member 260 to prevent the rod from rotating or moving axially within the inner member.

The connector 210 further includes a biasing member 276 that as illustrated is a coiled/torsional biasing member made of wire, although other types of biasing members may be used, such as for example a coiled metal band or elastic connection. The outer end 278 (FIG. 16) of the biasing member 276 is fixed in the biasing member housing portion 250 of the connector housing 240. The biasing member housing portion 250 may be closed by welding of a plate 280 (FIG. 15) and/or crimping the end portion of the housing. The inner end 274 (FIG. 16) of the biasing member 276 is fixed in the opening 272 in the biasing member receiving portion 270 of the inner member 260. The biasing member 276 thus acts between the connector housing 240 and the inner member 260. In other embodiments, the biasing member could be configured differently—for example, the biasing member could be a metal biasing member embedded in or coated with an elastomeric material. In still other embodiments, discussed below, a second biasing member may be provided.

As described below, the biasing member 276 provides resistance to relative rotation between the inner member 260 and the connector housing 240, resisting movement of the parts away from a neutral/unloaded or starting position, and biasing the parts back to the neutral/unloaded or starting position. This resistance is provided for movement in both directions of relative rotation, as shown by the arrows 282 and 284 in FIG. 19.

Figure 19:
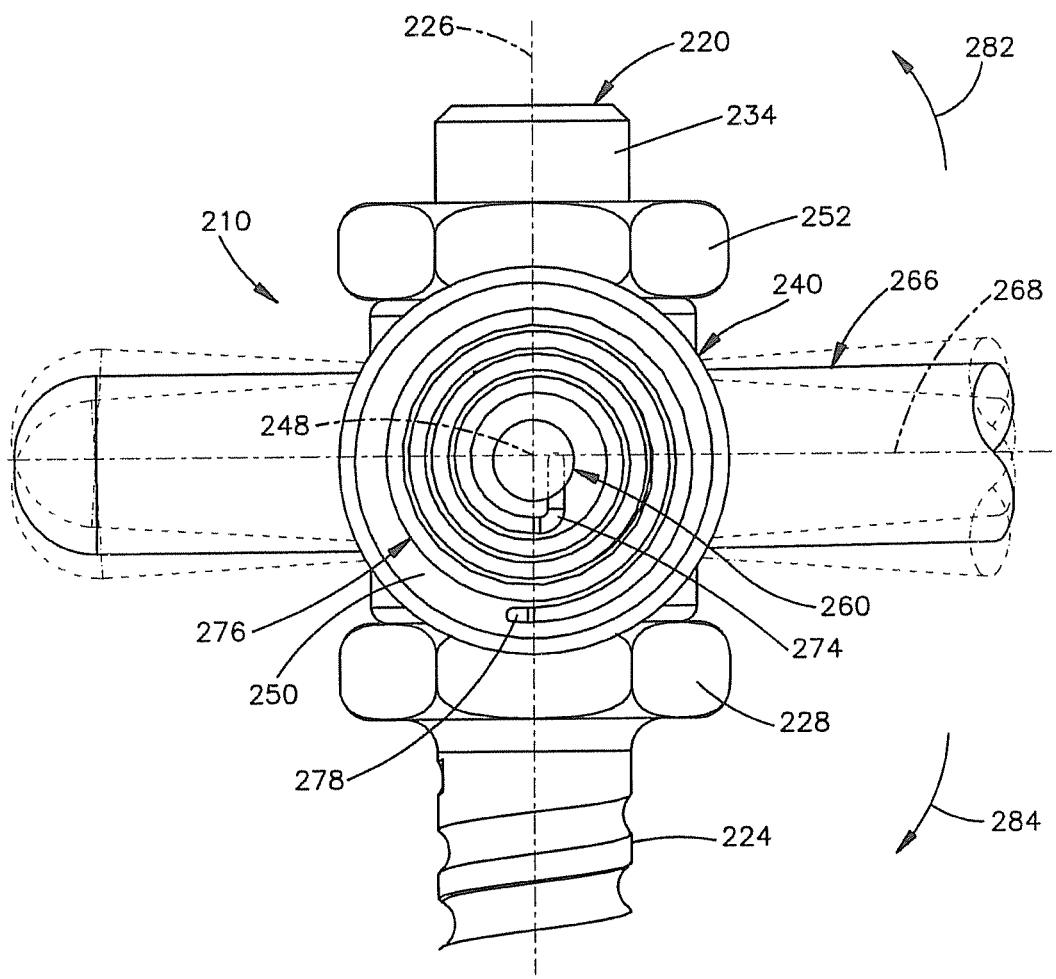
FIG. 19 is a front view of the connector shown in FIG. 15, wherein the connector is assembled and mounted to a screw.

Specifically, when the spine is flexed or extended, the vertebra 222 moves relative to the rod 266—for example, in a first direction as shown by the arrow 282 in FIG. 19. Force from the vertebra 222 is transmitted to the screw 220. The force on the screw 220 is transmitted to the connector housing 240. The connector housing 240 pivots relative to the inner member 260, about the pivot axis 248. Thus, the connector housing 240 pivots relative to the rod 266, which is fixed to the inner member 260.

The biasing member 276 resists the relative movement between the connector housing and the rod, about the axis 248, in the first direction shown by the arrow 282. The biasing member 276 provides an increasing resistance to relative movement between the inner member 260 and the connector housing 240, as the parts move farther. Thus, the biasing member 276 provides an increasing resistance to pivotal movement of the screw 220 relative to the rod 266.

The force applied by the biasing member 276 may increase sufficiently to act as a stop to limit such movement. Alternatively, an edge portion 284 (FIG. 16) of the rod support portion 244 of the connector housing 240 can act as a hard stop to definitively limit movement.

When the force on the screw 220 from the patient stabilizes or decreases, the return force of the biasing member 276 acts on the inner member 260 to help bias the parts of the connector 210 back to the starting position, in the direction indicated by the arrow 284 in FIG. 19.

The connector 210 may be configured to allow any desired range of movement within the physical constraints of the connector and associated devices. As one example, the connector 210 may be configured to allow for tip to 2 or 3 degrees of movement in either direction from the starting or neutral/unloaded position.

The amount of resistance and return force provided by the connector 210 may be adjusted by removing the biasing member 276 and replacing it with a stiffer or softer biasing member. This adjustment is facilitated by the fact that the biasing member housing portion 250 of the connector housing 240 is located outward of the rod 266 and thus readily accessible. In addition, the connector 210 as shown may be interchanged with another connector of the same or a different type, simply by removing the nut 252 and pulling the connector housing 240 axially off the screw 220.

In another embodiment, more than one biasing member is provided. Specifically, a first biasing member 276 (FIG. 18) is provided that provides resistance to rotation between the screw and the rod in a first direction. A second biasing member, shown in phantom at 276a in FIG. 18, is provided that provides resistance to rotation between the screw and the rod in the opposite direction. The engagement of the ends of the biasing members 276 and 276a, with the inner member 260 and with the biasing member housing 250, is configured so that each one of the biasing members provides resistance in only one direction of rotation, not both directions of rotation. Such a configuration may be used, for example, if the force curve of such biasing members is more predictable in one direction than the other.

As illustrated, the connector housing 240, inner member 260, biasing member 276, and plate 280 are made from titanium or a titanium alloy. However, some or all of the connector 210 components may be made from a variety of materials that are suitable for mammalian implantation, such as for example, but not limited to, polyethylene or polyurethane. Further, the screw 220 and the rod 266 may be made from a variety of materials that are suitable for mammalian implantation, such as titanium or a titanium alloy.

Figure 20:
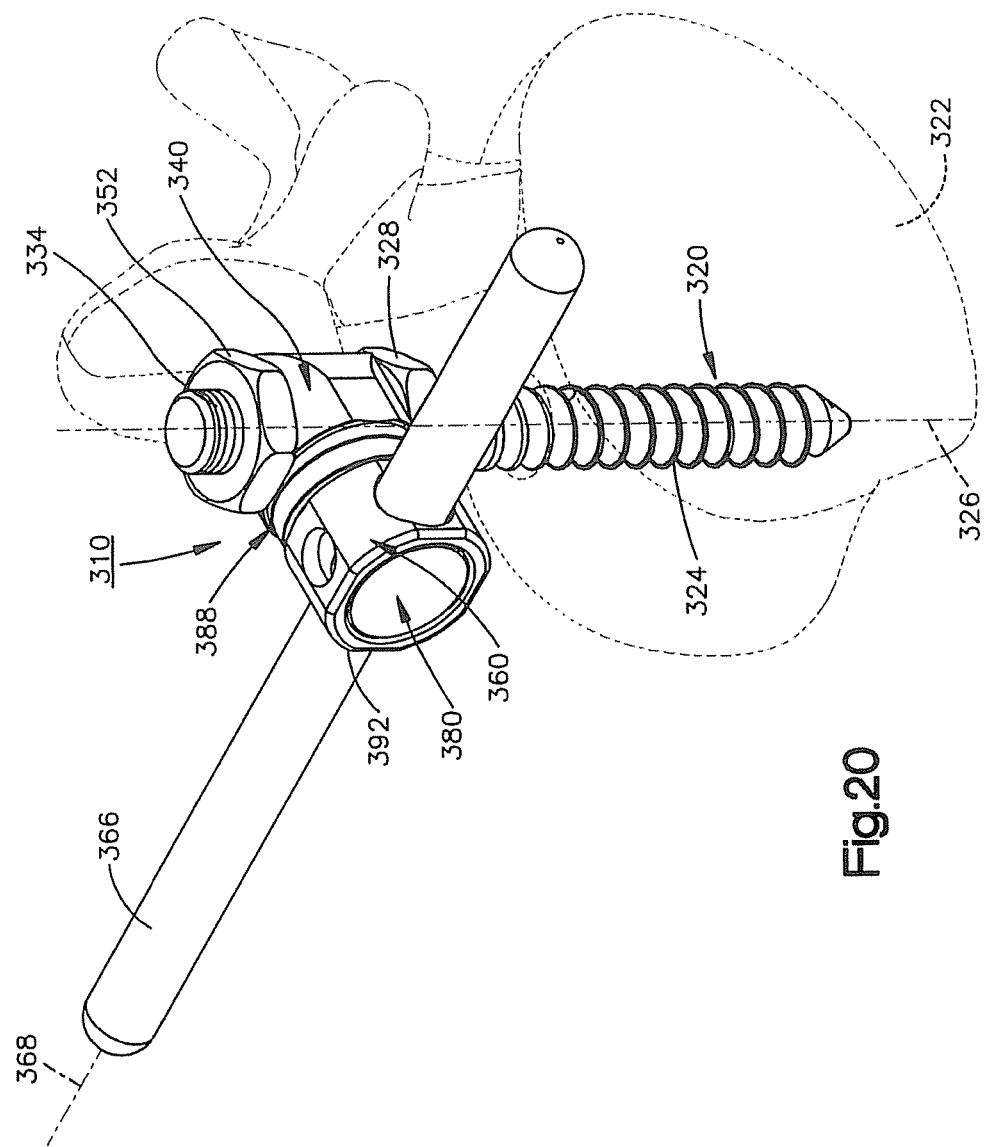
FIG. 20 is a perspective view of a connector according to another embodiment of the invention, wherein the connector is assembled and mounted to a screw.
Figure 21:
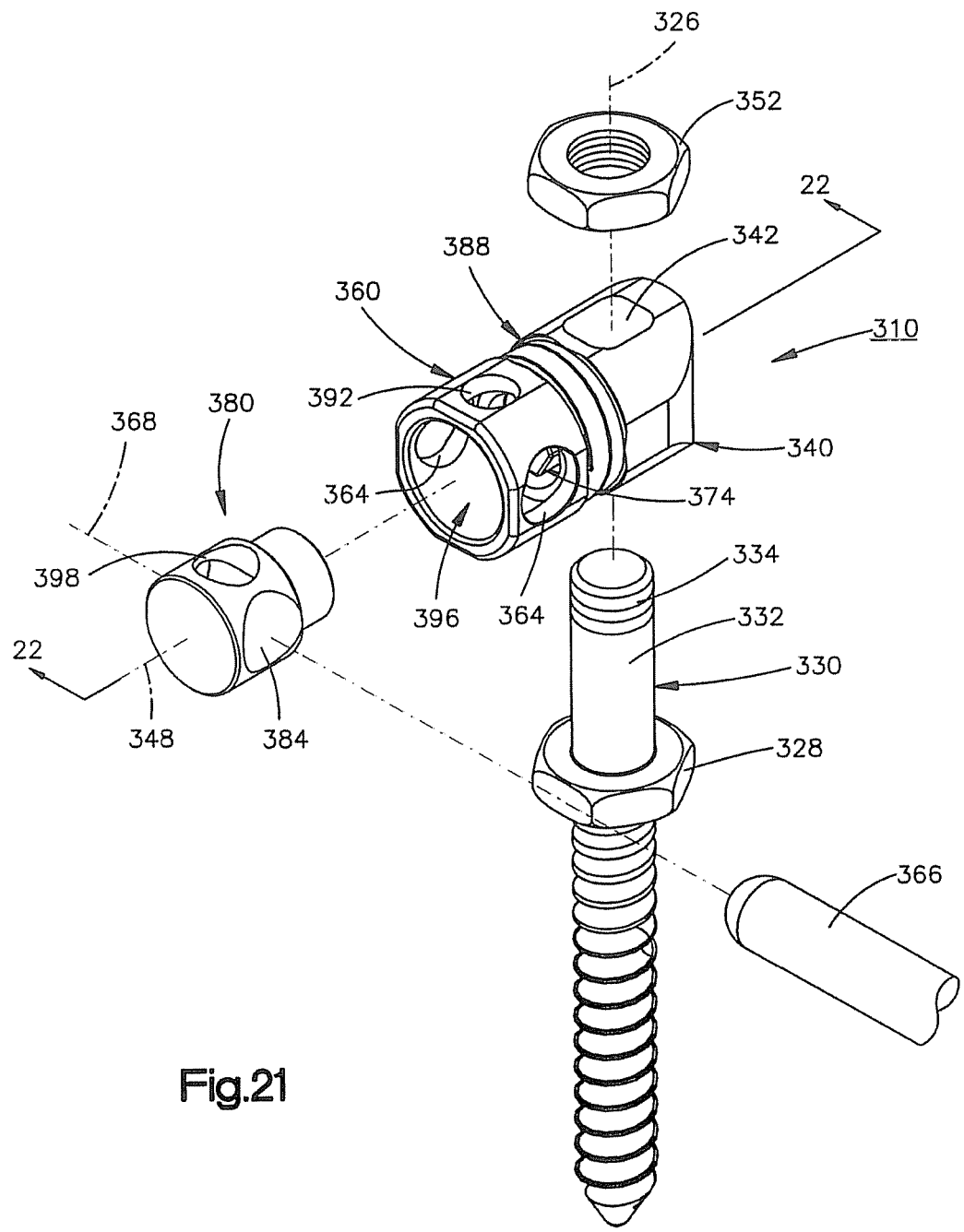
FIG. 21 is an exploded view of the connector shown in FIG. 20.
Figure 22:
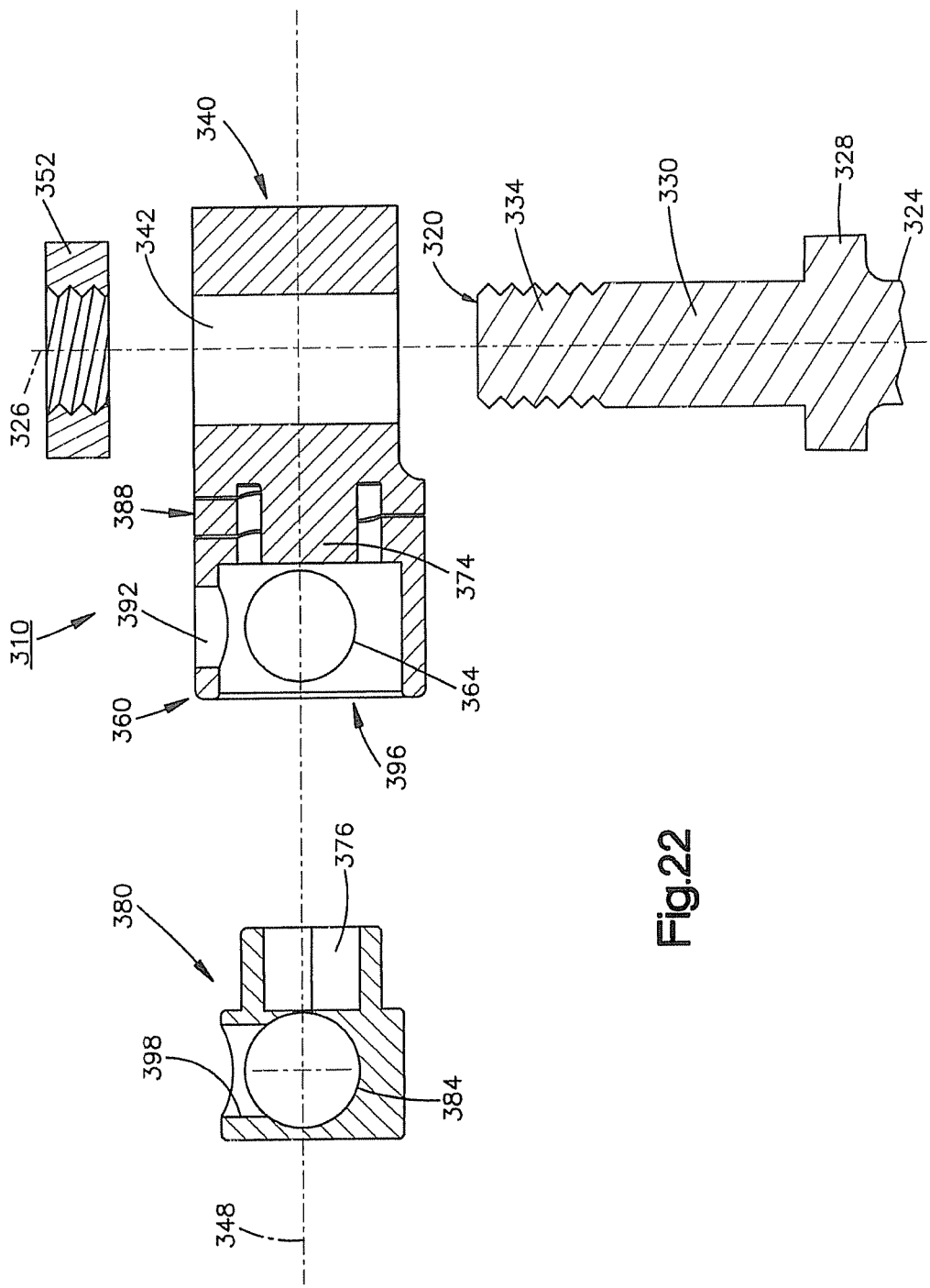
FIG. 22 is a exploded cross sectional view of the connector shown in FIG. 20.
Figure 23:
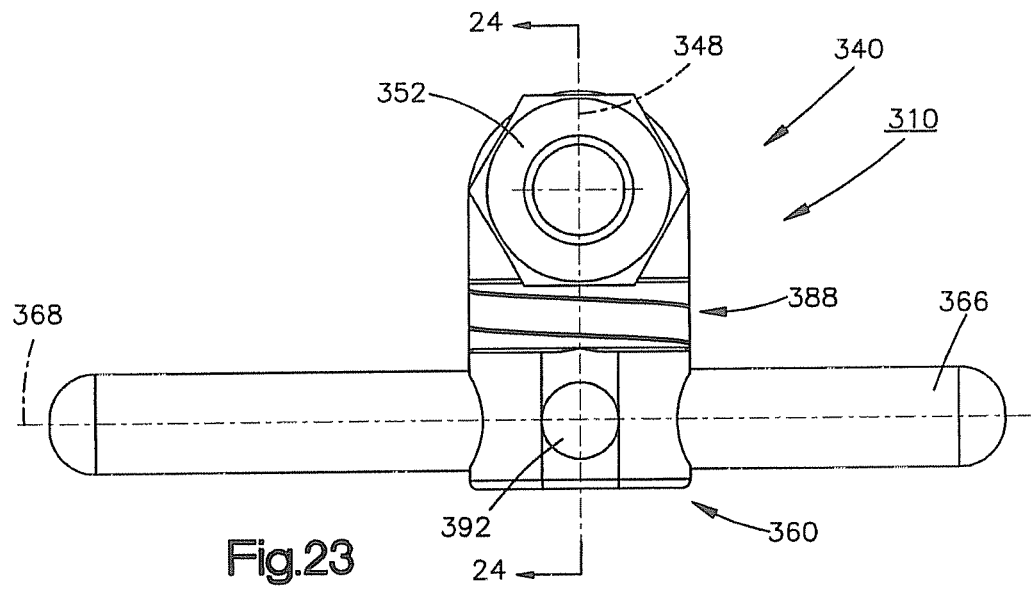
FIG. 23 is a top view of the connector shown in FIG. 20, wherein the connector is assembled and mounted to a screw.
Figure 24:
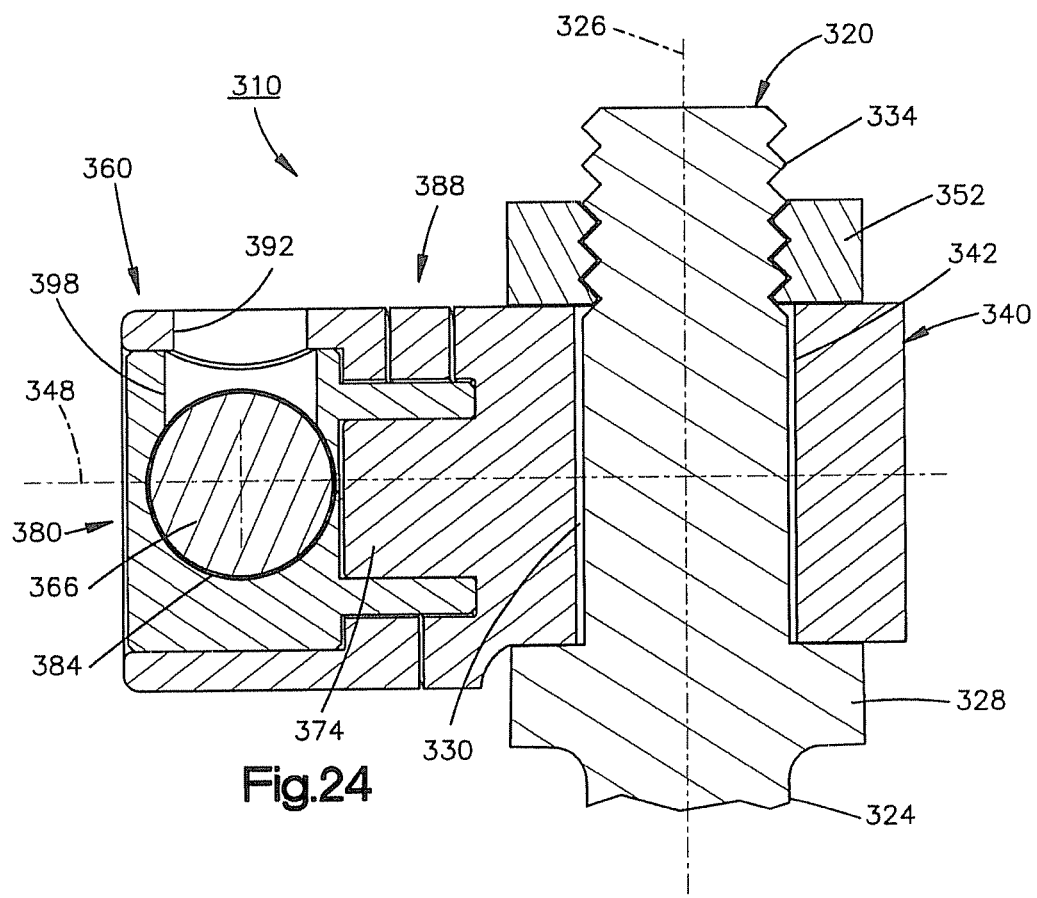
FIG. 24 is a cross sectional view of the connector shown in FIG. 20, wherein the connector is assembled and mounted to a screw.
Figure 25:
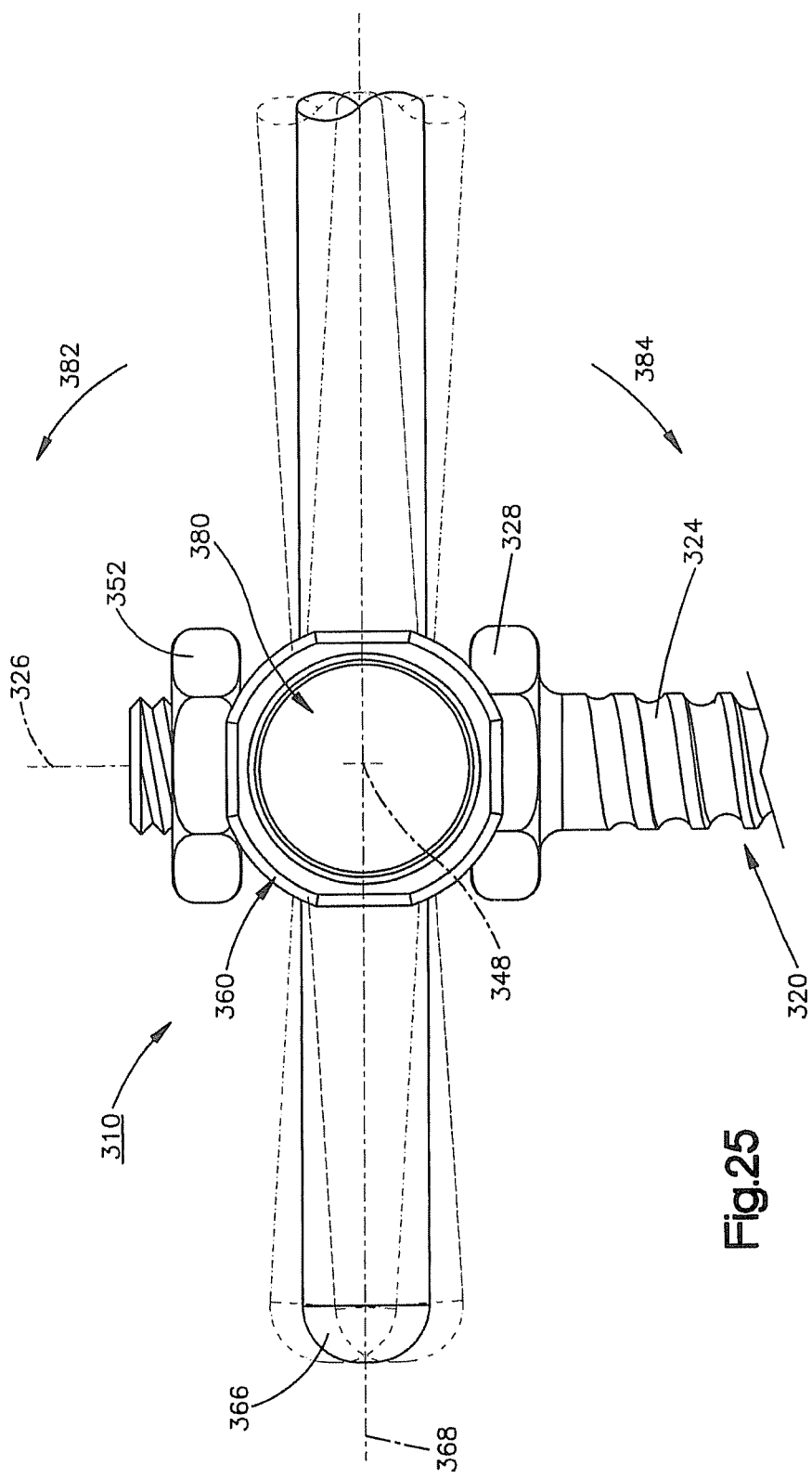
FIG. 25 is a front view of the connector shown in FIG. 20, wherein the connector is assembled and mounted to a screw.

FIGS. 20-27 illustrate another embodiment of the invention similar to the embodiment depicted in FIGS. 3-8. The connector 310 shown in FIG. 20 is adapted to work with a bone screw 320 in a vertebra shown schematically at 322, and with a member, such as a plate or rod, that extends to and connects with another vertebra (not shown) or with another bone tissue or soft tissue portion. The exemplary screw 320 depicted in FIGS. 20-25 has a first threaded portion 324 centered on an axis 326 of the screw, a flange 328 at the outer end of the first threaded portion 324, and a mounting portion 330 for mounting or supporting a first connector member 340 (FIG. 21). In the illustrated embodiment, the mounting portion 330 has a smooth, cylindrical outer surface 332 centered on the screw axis 326. A fastener 352 communicates with a second threaded portion 334 of the screw 320 to secure the first connector member 340 to the screw, blocking rotation of the member about the screw axis 326.

The connector 310 further comprises a biasing member 388 and a second connector member 360. As illustrated, the first connector member 340, the biasing member 388, and the second connector member 360 of the connector 310 are made as a unitary construction. The first connector member 340 (FIG. 21) has a mounting sleeve or mounting portion 342 that is received on the mounting portion 330 of the screw 320. The mounting portion 342 of the first connector member 340 supports the first connector member on the screw 320 for pivotal movement relative to the screw about the screw axis 326, before the first connector member is tightened down on the screw.

The second connector member 360 of the connector 310 has a bore 364 that extends radially through the second connector member and is adapted to receive a rod 366 (FIG. 21) therethrough. The bore 364 defines a rod axis 368 of the connector 310. In the illustrated embodiment, the second connector member 360 has set screw threads 392 for securing the rod 366 to the second connector member 360 to prevent the rod 366 from rotating or moving axially within the second connector member 360.

The biasing member 388 resists the rotation of the first connector member 340 relative to the second connector member 360 and helps to bias the parts of the connector 310 back to a starting position. As illustrated, the biasing member 388 is formed from a spiral cut between the first connector member 340 and the second connector member 360. The biasing member 388 and the second connector member 360 also have a chamber 396. As shown, the chamber 396 is centered on a pivot axis 348 and extends generally from the first connector member 340 through the biasing member 388 and the second connector member 360.

Figure 27:
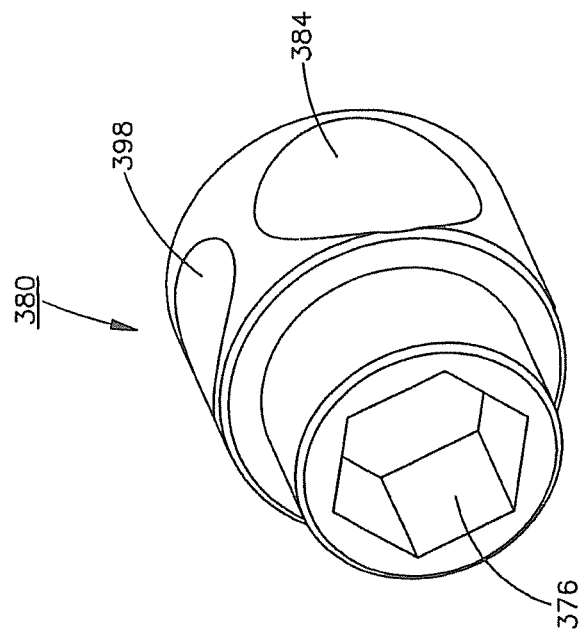
FIG. 27 is a perspective view of a stop of the connector shown in FIG. 20.
Figure 26:
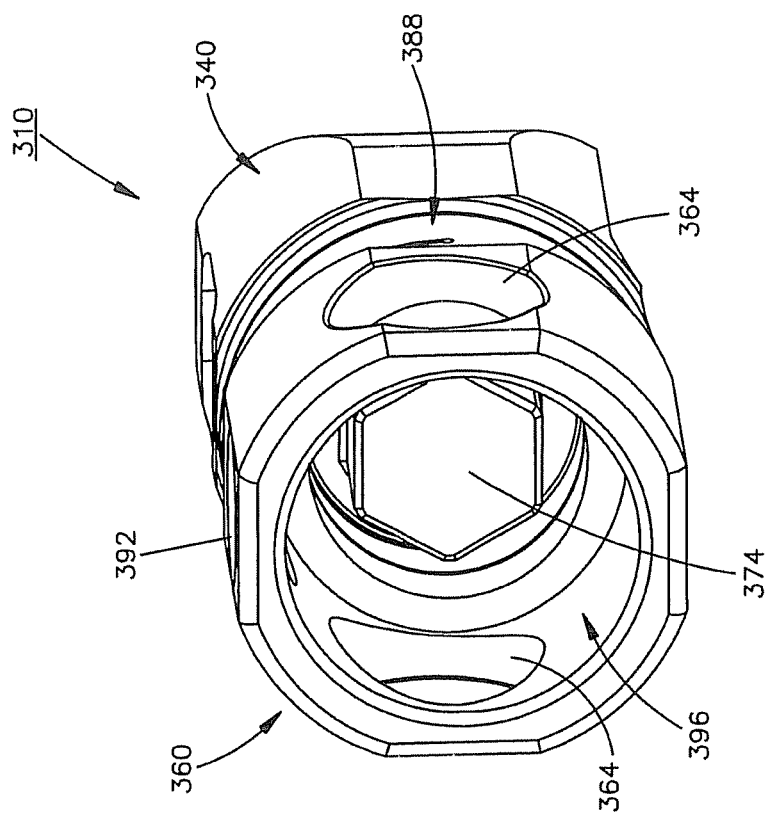
FIG. 26 is a perspective view the connector shown in FIG. 20.

As illustrated, the connector 310 comprises a stop 380 (FIG. 21) that limits the relative movement between the first connector member 340 and the second connector member 360. The stop 380 is cylindrical in shape and communicates with the chamber 396. The first connector member 340 has a shaft 374 centered on the pivot axis 348 of the connector 310 (FIG. 26) that extends into the chamber 396. As shown, the shaft 374 comprises a hexagonal outer surface and communicates with a bore 376 in the stop 380 (FIG. 27). The bore 376 of the stop 380 has a corresponding hexagonal inner surface that closely mates with the hexagonal outer surface of the shaft 374 to prevent the stop from rotating relative to the shaft 374 of the first connector member 340. However, the outer surface of the shaft 374 and the inner surface of the bore 376 may be any suitable non-circular shape known in the art capable of preventing the stop 380 from rotating relative to the shaft of the first connector member 340.

Similar to the bore 364 of the second connector member 360, a bore 384 extends radially through the stop 380. The bore 384 of the stop 380 is centered on the rod axis 368 of the connector 310 and allows the rod 366 to pass therethough. As shown, the diameter of the bore 384 of the stop 380 is slightly larger than the diameter of the bore 364 of the second connector member 360. As such, the rod 366 interferes with an edge portion of the bore 384 to limit the movement of the first connector member 340 relative to the second connector member 360 (see FIG. 24). Further, the stop 380 has an aperture 398 that allows access for the setscrew of second connector member 360 to secure the rod 366 in the bore 364 of the second connector member (see FIG. 24).

The range of rotation of the first connector member 340 relative to the second connector member 360 will vary depending on various factors. For example, the size and shape of the bore 384 of the stop 380 may vary creating different ranges of rotation. Further, the edge of the bore 384 may include a different material, such as an elastic material, that "cushions" the interference of the rod 366.

As illustrated, the first connector member 340, second connector member 360, biasing member 388, and stop 380 are made from titanium or a titanium alloy. However, some or all of the connector 310 components may be made from a variety of materials that are suitable for mammalian implantation, such as for example, but not limited to, polyethylene or polyurethane. Further, the screw 320 and the rod 366 may be made from a variety of materials that are suitable for mammalian implantation, such as titanium or a titanium alloy.

Similar to the connector 10 depicted in FIGS. 3-8, the biasing member 388 of the connector 310 provides resistance to relative rotation between the second connector member 360 and the first connector member 340, resisting movement of the parts away from a neutral/unloaded or starting position, and biasing the parts back to the neutral/unloaded or starting position. This resistance is provided for movement in both directions of relative rotation, as shown by the arrows 382 and 384 in FIG. 25. Further, the force applied by the biasing member 388 may increase sufficiently to act as a stop to limit such movement. As stated earlier, the interference of the bore 384 of the stop 380 and the rod 366 may also act as a stop to limit the pivotal movement of the screw 320, which is attached to the first connector member 340, relative to the rod 366.

The connector 310 may be configured to allow any desired range of movement within the physical constraints of the connector and associated devices. As one example, the connector 310 may be configured to allow for up to 2 or 3 degrees of movement in either direction from the starting or neutral/unloaded position.

The embodiments of the device described herein advantageously provide a reduction in bone-screw forces by enabling relative pivotal movement between the bone and the rod to provide a desired quality of motion. The pivotal connectors can help to stabilize the spine by resisting translational forces. The pivotal connectors can be customizable by offering biasing members of different stiffness, thus providing different degrees of motion preservation and load sharing. In addition, the biasing members may be fully enclosed, and as a result are not exposed to or interfering with any body substances when implanted.

The device has been described with reference to the preferred embodiments. Modification and alterations will occur to others upon a reading and understanding of this specification. It is intended to include all such modifications and alterations insofar as they come within the scope of the appended claims or the equivalents thereof.

It is claimed:

1. A surgical implant device that controls the relative movement between a first tissue portion and a second tissue portion, comprising:

a first connector member adapted to be connected for movement with the first tissue portion;

a second connector member adapted to be connected for movement with the second tissue portion;
a biasing member pivotally connecting the first connector member to the second connector member, the biasing member centered on a pivotal axis; and
wherein the biasing member resists the relative rotation between the first connector member and the second connector member;
wherein the first connector member further comprises a mounting portion having an aperture for connecting the first connector member to an anchoring device and the second connector member further comprises a mounting portion having an aperture for connecting the second connector member to a rod, wherein the rod is disposed substantially perpendicular to the pivotal axis; and
wherein the biasing member is coupled to the second member and disposed within the first connector member, and wherein a stop coupled to the second connector member is disposed about the biasing member.

2. The device of claim 1, wherein the anchoring device is a pedicle screw.

3. The device of claim 1, wherein the resistance to the movement of the first connector member relative to the second connector member increases as the first connector member rotates relative to the second connector member from an unloaded position.

4. The device of claim 1, wherein the stop limits the movement of the first connector member relative to the second connector member.

5. The device of claim 1, wherein the biasing member is a spring.

6. The device of claim 1, wherein the second connector member and the biasing member are a unitary construction and an end of the biasing member is connected to the first connector member.

7. The device of claim 6, wherein the end of the biasing member is welded in a chamber of the first connector member.

8. The device of claim 6, wherein the end of the biasing member is press fit in a chamber of the first connector member.

9. The device of claim 6, wherein the biasing member is formed by spiral cutting a portion of the second connector member.

10. The device of claim 6, wherein the second connector member comprises an outer member.

11. The device of claim 10, wherein the first connector member is rotatable relative to the outer member.

12. The device of claim 10, wherein the stop is coupled to the outer member.

13. The device of claim 12, wherein the stop comprises at least one projection of the outer member and at least one projection of the first connector member.

14. The device of claim 1, wherein the first connector member, the biasing member, and the second connector member are a unitary construction.

15. The device of claim 14, wherein the biasing member is formed by spiral cutting a portion of the device between the first connector member and the second connector member.

16. The device of claim 1, wherein the stop is internal to the device and comprises a bore, wherein an edge of the bore interferes with a rod connected to the second connector member.

17. The device of claim 1, wherein the device comprises at least one elastic band that resists the movement of the first connector member relative to the second connector member.

18. A surgical implant device that controls the relative movement between a first tissue portion and a second tissue portion, comprising:
a first connector member adapted to be connected for movement with the first tissue portion;
a second connector member adapted to be connected for movement with the second tissue portion;
a biasing member pivotally connecting the first connector member to the second connector member, the biasing member centered on a pivotal axis; and
wherein the biasing member resists the relative rotation between the first connector member and the second connector member;
wherein the first connector member further comprises a mounting portion having an aperture for connecting the first connector member to an anchoring device and the second connector member further comprises a mounting portion having an aperture for connecting the second connector member to a rod, wherein the rod is disposed substantially perpendicular to the pivotal axis;
wherein the first connector member, the biasing member, and the second connector member are a unitary construction, wherein the biasing member is formed by spiral cutting a portion of the device between the first connector member and the second connector member; and
wherein the device comprises a stop limiting the movement of the first connector member relative to the second connector member, and wherein the stop is internal to the device and comprises a bore, wherein an edge of the bore interferes with a rod connected to the second connector member.

* * * * *